United States Patent
Troxler et al.

(10) Patent No.: US 9,612,346 B2
(45) Date of Patent: Apr. 4, 2017

(54) NUCLEAR GAUGES AND METHODS OF CONFIGURATION AND CALIBRATION OF NUCLEAR GAUGES

(71) Applicant: Troxler Electronic Laboratories, Inc., Research Triangle Park, NC (US)

(72) Inventors: Robert Ernest Troxler, Raleigh, NC (US); Dirk M. Steckmann, Cary, NC (US); Donald E. Weger, Wendell, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

(21) Appl. No.: 14/748,171

(22) Filed: Jun. 23, 2015

(65) Prior Publication Data
US 2015/0293240 A1   Oct. 15, 2015

Related U.S. Application Data

(60) Continuation of application No. 13/414,680, filed on Mar. 7, 2012, now Pat. No. 9,063,062, which is a
(Continued)

(51) Int. Cl.
*G01T 7/00* (2006.01)
*G01D 18/00* (2006.01)
(Continued)

(52) U.S. Cl.
CPC ........... *G01T 7/005* (2013.01); *G01D 18/008* (2013.01); *G01N 23/09* (2013.01); *G01N 23/06* (2013.01);
(Continued)

(58) Field of Classification Search
CPC ....... G01T 7/005; G01D 18/008; G01N 23/06
See application file for complete search history.

(56) References Cited

U.S. PATENT DOCUMENTS

| 4,587,623 | A | * | 5/1986 | Regimand | ................ | G01V 5/02 |
| | | | | | | 250/252.1 |
| 4,791,656 | A | * | 12/1988 | Pratt, Jr. | .............. | G01N 23/203 |
| | | | | | | 250/252.1 |

(Continued)

OTHER PUBLICATIONS

USPTO, Notice of Allowance and Fees Due for U.S. Appl. No. 12/348,821, Dec. 23, 2011, US.
(Continued)

*Primary Examiner* — Casey Bryant
(74) *Attorney, Agent, or Firm* — NK Patent Law, PLLC

(57) ABSTRACT

A method for calibrating a nuclear gauge of the having a source includes providing a nuclear gauge comprising a radiation source, the radiation source being coupled with a computing system with a machine readable program stored thereon containing a calibration routine. An operator places the gauge on one or more specified blocks to adjust the source within each block to one or more specified positions to initiate a count. The method includes determining that the source is at each position before each count begins, adjusting the counting times before each count begins by the program on the nuclear gauge based on each position of the source to obtain calibration information, obtaining counts at each position, storing the counts within the computing system of the nuclear gauge, and calculating for each position calibration coefficients.

23 Claims, 38 Drawing Sheets

Related U.S. Application Data division of application No. 12/348,821, filed on Jan. 5, 2009, now Pat. No. 8,164,048.

(60) Provisional application No. 61/010,191, filed on Jan. 4, 2008, provisional application No. 61/010,022, filed on Jan. 4, 2008, provisional application No. 61/010,103, filed on Jan. 4, 2008.

(51) Int. Cl.
*G01N 23/09* (2006.01)
*G01N 23/06* (2006.01)
*G01N 23/203* (2006.01)

(52) U.S. Cl.
CPC ....... *G01N 23/203* (2013.01); *Y10T 29/49826* (2015.01)

(56) References Cited

U.S. PATENT DOCUMENTS

| | | | | |
|---|---|---|---|---|
| 4,864,842 | A * | 9/1989 | Regimand | G01N 23/09 250/252.1 |
| 5,151,601 | A * | 9/1992 | Regimand | G01N 23/025 250/390.04 |
| 5,923,726 | A | 7/1999 | Regimand | |
| 6,050,725 | A | 4/2000 | Regimand | |
| 6,369,381 | B1 * | 4/2002 | Troxler | G01N 23/223 250/252.1 |
| 7,373,504 | B1 | 5/2008 | Belgaied et al. | |
| 7,605,366 | B2 | 10/2009 | Dep et al. | |
| 7,820,960 | B2 | 10/2010 | Troxler | |
| 7,872,222 | B1 | 1/2011 | Dep et al. | |
| 7,928,360 | B2 | 4/2011 | Troxler | |
| 7,962,416 | B1 | 6/2011 | Durbin et al. | |
| 8,071,937 | B2 | 12/2011 | Troxler | |
| 2002/0149617 | A1 | 10/2002 | Becker | |
| 2004/0073382 | A1 | 4/2004 | Troxler et al. | |
| 2004/0095154 | A1 | 5/2004 | Lundstrom et al. | |
| 2004/0260504 | A1 | 12/2004 | Bienvenu et al. | |
| 2007/0216573 | A1 | 9/2007 | Handermann et al. | |
| 2008/0004798 | A1 * | 1/2008 | Troxler | A01K 15/023 702/187 |
| 2009/0250599 | A1 | 10/2009 | Bartlett et al. | |

OTHER PUBLICATIONS

USPTO, Non-Final Rejection for U.S. Appl. No. 13/414,680, May 30, 2012, US.

USPTO, Final Rejection for U.S. Appl. No. 13/414,680, Feb. 8, 2013, US.

USPTO, Non-Final Rejection for U.S. Appl. No. 13/414,680, Jul. 23, 2013, US.

USPTO, Final Rejection for U.S. Appl. No. 13/414,680, Jan. 16, 2014, US.

USPTO, Non-Final Rejection for U.S. Appl. No. 13/414,680, Aug. 18, 2014, US.

* cited by examiner

FIG. 18B     FIG. 18C

NUCLEAR GAUGES AND METHODS OF CONFIGURATION AND CALIBRATION OF NUCLEAR GAUGES

RELATED APPLICATIONS

The presently disclosed subject matter claims the benefit of U.S. patent application Ser. No. 13/414,680 filed on Mar. 7, 2012, which claims the benefit of U.S. patent application Ser. No. 12/348,821 filed on Jan. 5, 2009, which claims the benefit of U.S. Provisional Patent Application Ser. Nos. 61/010,103, 61/010,022, and 61/010,191, all filed Jan. 4, 2008; the disclosures of which are incorporated herein by reference in their entirety.

TECHNICAL FIELD

The present subject matter generally relates to an apparatus and method for determining the density and/or moisture of materials and, more particularly, relates to nuclear gauges used in measuring the density and/or moisture of construction-related materials.

BACKGROUND

Nuclear radiation gauges have been widely used for measuring the density and moisture of soil and asphaltic materials, or other construction material. As used herein, construction material is any materials used in building roads or foundational structures including, but not limited to soils, asphalts, asphalt-like materials, concrete, composite materials, or the like. Such gauges typically include a source of gamma radiation which directs gamma radiation into the test material, and a radiation detector located adjacent to the surface of the test material for detecting radiation scattered back to the surface. From this detector reading, a determination of the moisture and density of the material can be made.

These gauges are generally designed to operate either in a "backscatter" mode or in both a backscatter mode and direct transmission mode. In gauges capable of direct transmission mode, the radiation source is vertically moveable from a backscatter position, where it resides within the gauge housing, to a series of direct transmission positions, where it is inserted into small holes or bores in the test specimen.

Many of the gauges commonly in use for measuring density of soil, asphalt and other materials are most effective in measuring densities of materials over depths of approximately 3-12 inches. However, with the increase in cost of paving materials, the practice in maintaining and resurfacing paved roadbeds has become one of applying relatively thin layers or overlays having a thickness of one to three inches. With layers of such a thickness range, many density gauges are ineffective for measuring the density of the overlay because the density reading obtained from such gauges reflects not only the density of the thin layer, but also the density of the underlying base material.

Nuclear gauges capable of measuring the density of thin layers of materials have been developed by Troxler Electronic Laboratories, Inc. of Research Triangle Park, N.C. For example, thin layer density gauges are disclosed in U.S. Pat. Nos. 4,525,854, 4,701,868, 4,641,030, 6,310,936 and 6,442,232, all of which are incorporated herein by reference in their entirety. Some of the gauges disclosed in the above-referenced patents are referred to as "backscatter" gauges because the radiation source does not move outside the gauge housing, which is necessary for measurement in the direct transmission mode. In some of the gauges disclosed in the above-referenced patents, the gauge can have radiation sources that can also be extended outside of the gauge housing and into the material to be measured in a direct transmission mode. Typically, the source rods can extend up to about 12 inches.

As disclosed in the above patents, the preferred method of measuring the density of thin layers of materials, such as asphalt, is nondestructive and uses the backscatter mode. One method requires two independent density measurement systems. The geometry of these two measurement systems must be configured with respect to one another and with respect to the medium being measured in such a manner that they measure two different volumes of material. The two different volumes are not mutually exclusive insofar as they partially overlap one another. Measurement accuracy depends upon a larger portion of the volume measured by one of the measurement systems being distributed at a lower depth beneath the gauge than the volume measured by the other measurement system. This is accomplished by placing one radiation detection system in closer spatial proximity to the radiation source than the other detection system. Another volume specific measurement is typically used in soils and requires drilling a small hole in the material under test. This method is referred to as the direct transmission mode To determine the positioning of the source rod during use normally includes a visual inspection of the location of the source rod relative to an index rod and/or the height of the portion of the source rod extending out of the gauge housing. Such determination can be problematic and inaccurate. Contact strips whose resistance varies with position have also been used to detect the length that the source rod has moved. These strips often wear out.

Preparation for configuring a gauge can be time consuming. For gauges used in the past, each type of gauge would be configured differently so that there would be multiple configuration programs for gauges. Thus, each type of gauge could have a separate configuration program written for it.

Also, as known in the art, the calibration of a nuclear gauge, for example, a 12-position nuclear gauge is time consuming, and many quality control checks have to be implemented. For instance, programs over the years have been developed that analyze the calibration curves to find statistical variations in the gauge. For example, the typical calibration constants, count rate, precision and slope as a function of density of each gauge, along with their standard deviations, have been determined. These parameters are an important part of the diagnostics of the health of a gauge. Currently, only at the factory can this sort of diagnostics be accomplished. In the factory, external computer networks are wired to each calibration bay, the data is transferred by wire from the instrument to the external computer, where computer programs known in the art are used to curve fit, transfer the coefficients, store the coefficients to the gauge, and quality control check each measurement for deviations out of the standard expected values.

There remains a need in the art for a nuclear gauge capable of operating in backscatter mode and/or direct transmission mode, and which is suitable for efficiently measuring the density and moisture of construction material.

SUMMARY

In accordance with this disclosure, nuclear gauges for determining the density and/or moisture of materials and methods of configuration and calibration of nuclear gauges are provided. It is, therefore, an object of the present disclosure to provide nuclear gauges used in measuring the density and/or moisture of construction-related materials and methods for configuration of the gauges and methods of calibration of the gauges. This and other objects as may become apparent from the present disclosure are achieved, in whole or in part, by the subject matter described herein.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE DRAWINGS

A full and enabling disclosure of the present subject matter including the best mode thereof to one of ordinary skill in the art is set forth more particularly in the remainder of the specification, including reference to the accompanying figures, in which:

FIGS. 18A-18C illustrate different views of an embodiment of a replaceable sliding guide for use in a nuclear gauge according to the present subject matter;

DETAILED DESCRIPTION

Reference will now be made in detail to the description of the present subject matter, one or more examples of which are shown in the figures. Each example is provided to explain the subject matter and not as a limitation. In fact, features illustrated or described as part of one embodiment can be used in another embodiment to yield still a further embodiment. It is intended that the present subject matter cover such modifications and variations.

Nuclear Gauge Apparatus

Figure 1:
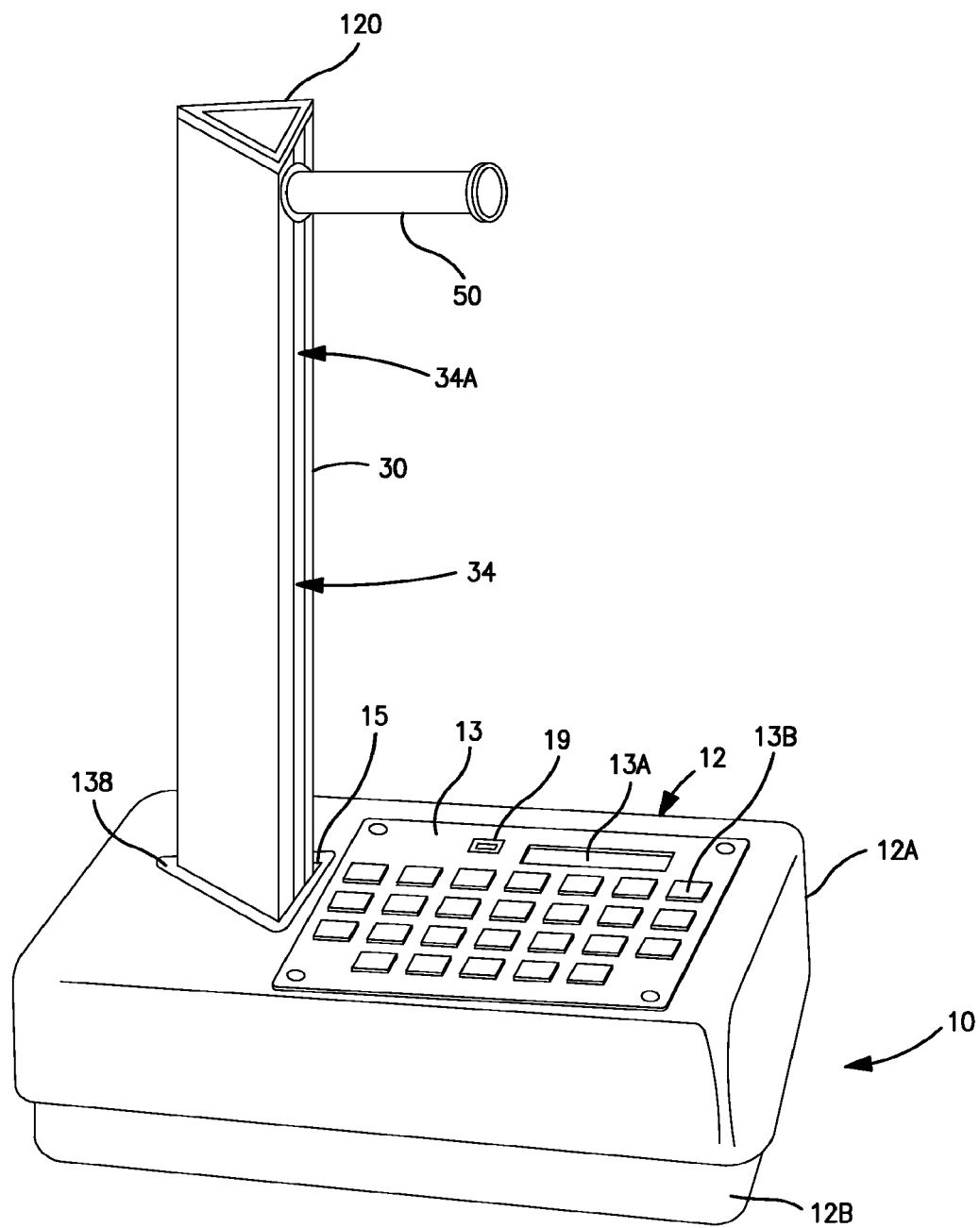
FIG. 1 illustrates a perspective view of an embodiment of a nuclear gauge according to the present subject matter.
Figure 2:
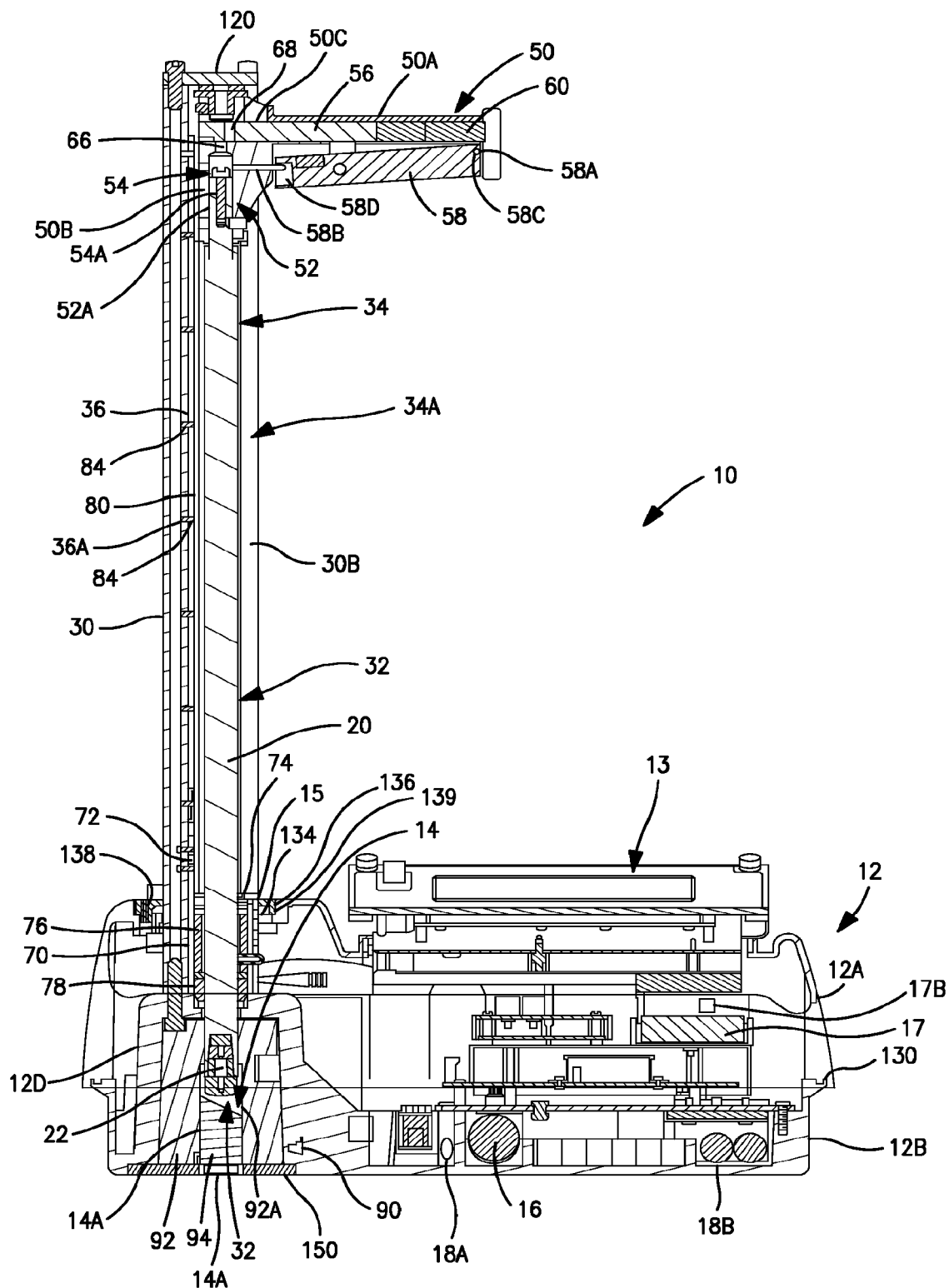
FIG. 2 illustrates a vertical cross-sectional view of the nuclear gauge illustrated in FIG. 1.
Figure 3:
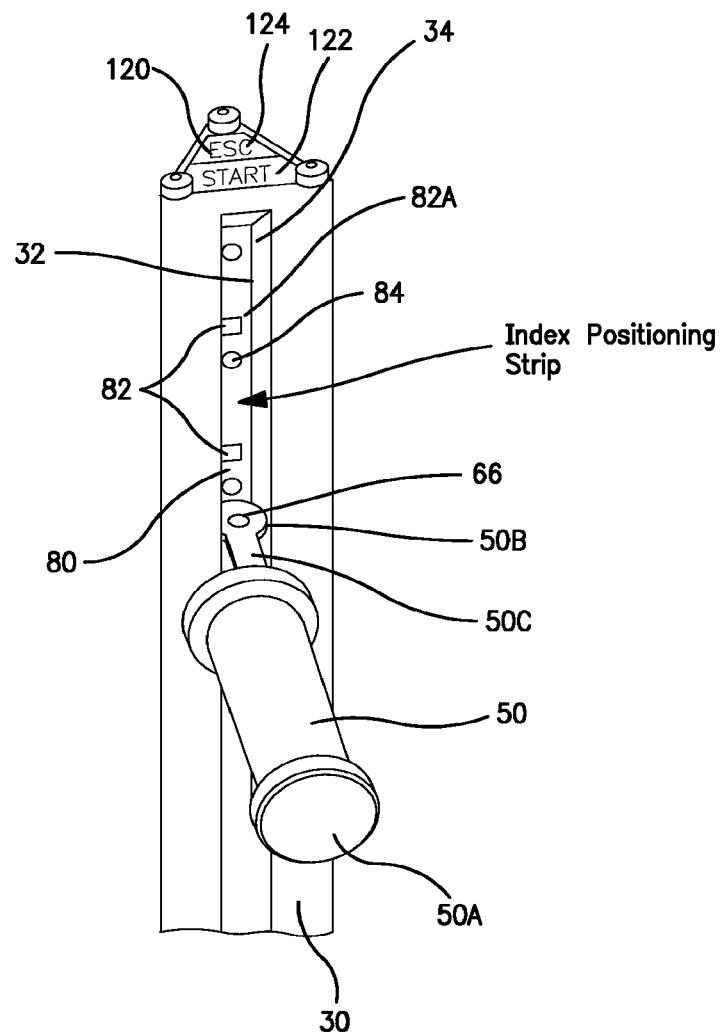
FIG. 3 illustrates a perspective view of a portion of the nuclear gauge illustrated in FIG. 1.

FIGS. 1 and 2 illustrate a nuclear gauge, generally designated 10. Different aspects and elements of gauge 10 will be briefly described with a more detailed description of the different elements provided further below. The nuclear gauge can be a density gauge, a bulk density gauge, a thin overlay gauge, a thin layer gauge, or a combination thereof.

By way of example to explain the present subject matter, the gauge 10 depicted in the figures is a thin layer gauge. However, as stated above, the gauge 10 can be other configurations of nuclear gauges. The gauge 10 can be capable of accurately measuring the density of materials, for example, thin layers of materials such as asphalt, through the use of a scattered radiation that is detected by radiation detectors. The gauge 10 can operate in both backscatter and direct transmission modes. The gauge 10 can include a gauge housing 12 and a tower, or source rod housing, 30. The gauge housing 12 and the tower 30 can form a vertical conduit 32 that extends through both gauge housing 12 and tower 30. For example, the gauge housing 12 can have a vertical cavity 14 therein and the tower 30 can include a vertical channel 34 therein that can be aligned to create the vertical conduit 32. For instance, the gauge housing 12 can include a top cover 12A and a base 12B. The base 12B can include the vertical cavity 14 therethrough. The top can include an opening 15 through which the tower 30 can pass. The tower 30 can be disposed on the base 12B of the gauge housing 12 so that the vertical channel 32 aligns with the vertical cavity 14 to form a vertical conduit 34 through the tower 30 and the gauge housing 12.

The gauge 10 can include a user interface 13 that is located on the top cover 12A of the gauge housing 12. The user interface 13 can be in communication with a computing system, such as central processing unit (CPU) 17, that controls the gauge 10 and runs the associated tests. For example, the user interface 13 can include a screen 13A and keypad 13B that can be used to input the parameters of the tests to be run on the nuclear gauge 10.

Figure 14:
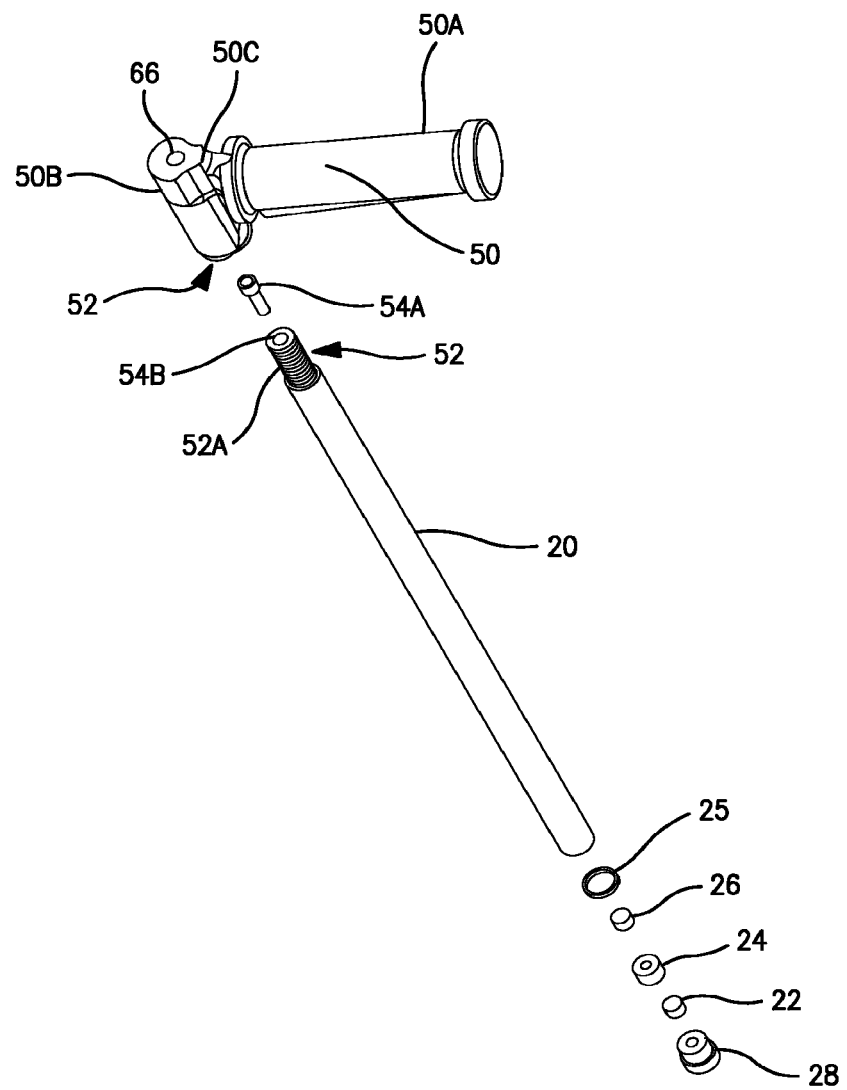
FIG. 14 illustrates an exploded view of an embodiment of a source rod and handle according to the present subject matter.
Figure 15:
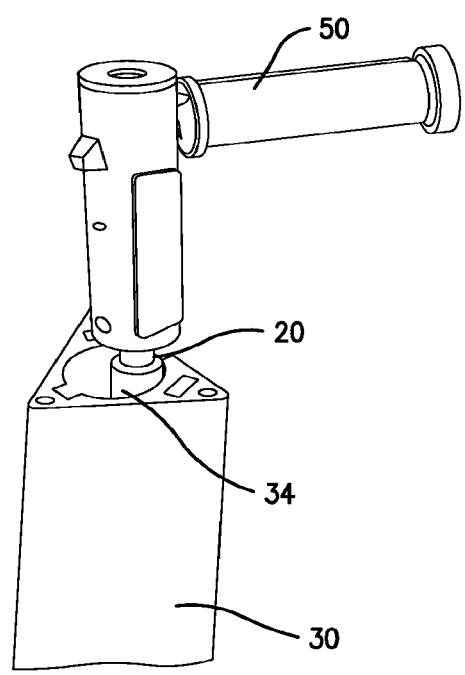
FIG. 15 illustrates a perspective view of an embodiment of a source rod being inserted a support tower, or source rod housing, according to the present subject matter.

The gauge 10 can include a vertically moveable source rod 20 containing a radiation source 22 in a distal end thereof. As shown in FIG. 14, the source rod 20 can include a spacer 24, a ring weld 25, a source spring 26 and a source plug 28. The radiation source 22 may be any suitable radiation source, such as $^{137}$Cs radiation source or $^{60}$Co. The source rod 20 can reside in the vertical conduit 32 created by the vertical channel 34 of the tower 30 and the vertical cavity 14 in the gauge housing 12.

The gauge 10 can include at least one density measurement system that utilizes at least one radiation detector. For example, as shown in FIG. 2, the gauge 10 can include two separate density measurement systems. The geometry of these two measurement systems is configured with respect to one another and with respect to the medium being measured in such a manner that they measure two different volumes of material. The two different volumes are not mutually exclusive insofar as they partially overlap one another. Measurement accuracy depends upon a larger portion of the volume measured by one of the measurement systems being distributed at a lower depth beneath the gauge than the volume measured by the other measurement system. This is accomplished by placing one radiation detection system in closer spatial proximity to the radiation source than the other detection system. To accomplish this, the gauge 10 includes a first radiation detector 18A and a second pair of radiation detectors 18B, wherein the first radiation detector 18A is located in closer spatial proximity to the radiation source 22. The radiation detectors, 18A and 18B, for example, may be any type of gamma ray radiation detector. For instance, the radiation detectors, 18A and 18B, can include preferably Geiger Mueller tubes, but can also include scintillation detectors, or proportional counters. The radiation detectors, 18A and 18B, can be located adjacent to the base 12B of the gauge housing 12. The gauge 10 can also include a moisture detector 16 that can use to measure the moisture of such construction material.

The gauge 10 can also include a handle 50 that is secured to the source rod 20 for vertically extending and retracting the source rod 20. The handle 50 along with a guide and sealing system 70 facilitate the guidance of the source rod 20 through the vertical conduit 32 created by the vertical channel 34 in the tower 30 and the vertical cavity 14 in the base 12B of the gauge housing 12. The handle 50 can be used to move the source rod to a plurality of predetermined source rod locations so as to change the spatial relationship between the radiation source and the at least one radiation detector. The handle 50 includes a coarse adjustment mechanism 52 and a fine adjustment element 54 for adjusting the height of the source rod 20 for positioning the radiation source 22 relative to the radiation detectors 18A, 18B to provide proper measurement at the different predetermined source rod locations. In particular, the source location at backscatter is extremely important and should be very precise.

To provide the predetermined source rod locations, an indexing mechanism can be provided. For example, as shown in FIGS. 2-6, an index positioning strip 80 can be placed in the tower 30 that can be engaged by the handle 50 to hold the source rod 20 at a predetermined source rod location. The index positioning strip 80 can include index holes 82 therein. The index holes 82 can serve as notches that the handle 50 engages as will be explained in more detail below. The index holes 82 can be uniformly spaced apart from each other. For example, the index holes 82 can be spaced apart at interval distances of about one inch, about two inches or about three inches.

The tower 30 can include an indexing groove 36 that is adjacent and opens into the vertical channel 34. The index positioning strip 80 can be secured in the indexing groove 36. The index positioning strip 80 can have apertures 84 for accepting fasteners 84, such as screws, rivets or the like that engage the tower 30. The index positioning strip 80 having index holes 82 therein can be securable at a designated location within the vertical channel 34 of the tower 30 to create the notches. Further, the index positioning strip 80 can be adjustable within the tower 30.

A depth strip 100, as shown in FIGS. 9-12, can be positioned in the tower 30 and can provide a non-contact measurement of the source position. The depth strip can use optical sensors, such as optical range finder sensors, acoustic sensors, magnetic sensors and the like to provide non-contact measuring of the positioning of the source rod. For example, the depth strip can include a plurality of Hall Effect depth sensors 102. Each of the depth sensors can be associated with at least one of the source rod positions. The positioning of the source rod 20 at one of the source rod positions can activate one of the Hall Effect depth sensors 102 for detecting the source rod position of the source rod 20. The depth strip 100 can comprise a source rod position detection circuitry 104 adapted for detecting activation of the depth sensors to determine a current position of the source rod 20. This position can be relative from one another, or preferably absolute indicators.

The depth strip 100 can include a parting line 100A with the depth strip 100 being convertible from a 12-inch unit to an 8-inch unit along the parting line 100A. Another parting line can be included on the depth strip to create a depth strip that can be used in a backscatter only gauge. To house the depth strip 100, the tower 30 can include a measurement compartment 38. Depending on the type of depth strip 100, the measurement compartment 38 can be a separate channel or passageway for housing the depth strip.

Once the nuclear gauge 10 is assembled, the computing system, for example, the CPU 17, can be configured to operate with a plurality of options. Thereby, the nuclear gauge 10 can be configurable to operate in a plurality of settings. The computing system 17 can be configured to enable and to disable the settings of the nuclear gauge 10. A nuclear gauge configuration system in communication with the computing system of the nuclear gauge 10 can also be provided. At the nuclear gauge configuration system, commands can be communicated to the computing system 17 of the nuclear gauge 10 for one of enabling and disabling the settings of the nuclear gauge 10.

To also ensure proper measurements using the gauge 10, a method for calibrating a nuclear gauge is disclosed. The method includes providing a nuclear gauge 10 adapted to be remotely calibrated via encrypted calibration communications. The nuclear gauge 10 can include a command line interpreter function adapted for receiving calibration commands. Further, the method includes providing a nuclear gauge calibration system in communication with the computing system 17 of the nuclear gauge 10. The nuclear gauge calibration system is adapted to interrogate the nuclear gauge for calibration information. The method includes communicating, at the nuclear gauge calibration system, encrypted commands to the nuclear gauge for calibrating the nuclear gauge.

The gauge 10 also includes a radiation shield assembly 90 as shown in FIGS. 2 and 17-24. The radiation shield assembly 90 includes a safety shield 92 that is coaxially mounted in the base 12B of the gauge housing. The safety shield 92 helps to define the vertical cavity 14 in the base 12B of the gauge housing 12. For example, the base 12B is formed to create a shield housing 12D through which an opening passes. The safety shield 92 has a passage 92A passing therethrough. The safety shield 92 fits into the shield housing 12D so that the opening in the shield housing 12D aligns with the passage 92A in the safety shield 92. A set screw 93 can secure the safety shield 92 in place by screwing the set screw 93 into a screw hole 93A in the shield housing 12D. The aligned opening in the shield housing 12D and the passage 92A through the safety shield 92 can create the vertical cavity 14.

Figure 21:
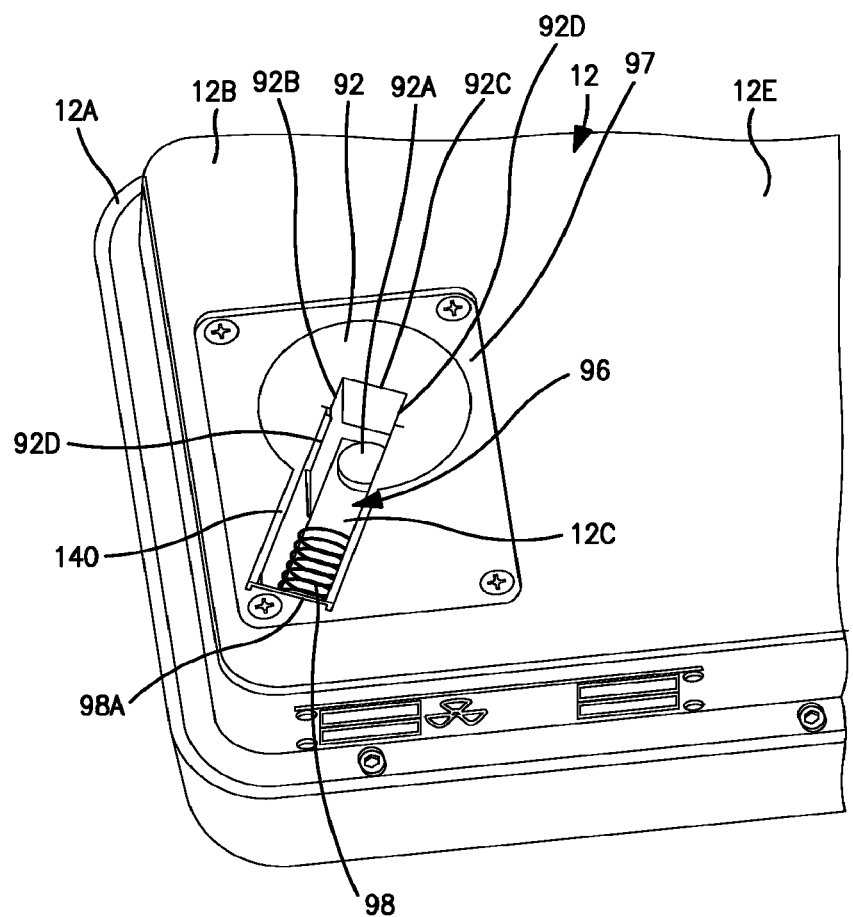

The radiation shield assembly 90 also includes a sliding block 94 that is positionable to move laterally between two positions relative to the safety shield 92. The sliding block 94 can reside in a first position blocking a distal end of the vertical cavity 14 such that radiation is shielded from exiting the cavity. The sliding block 94 can also reside in a second position adjacent the vertical cavity. In the second position the source rod 20 can move vertically through the radiation shield assembly 90 and the base 12B of the gauge housing 12. The base 12B of the gauge housing 12 and the safety shield 92 can define a track 96 configured to receive the sliding block 94 and guide movement of the sliding block 94. For example, a shield track segment 92B can be defined in the safety shield 92 that comprises at least a portion of the track 96. The shield track segment 92B and the passage 92A can intersect and merge at the lower end of the safety shield 92 as shown in FIG. 21.

Figure 22:
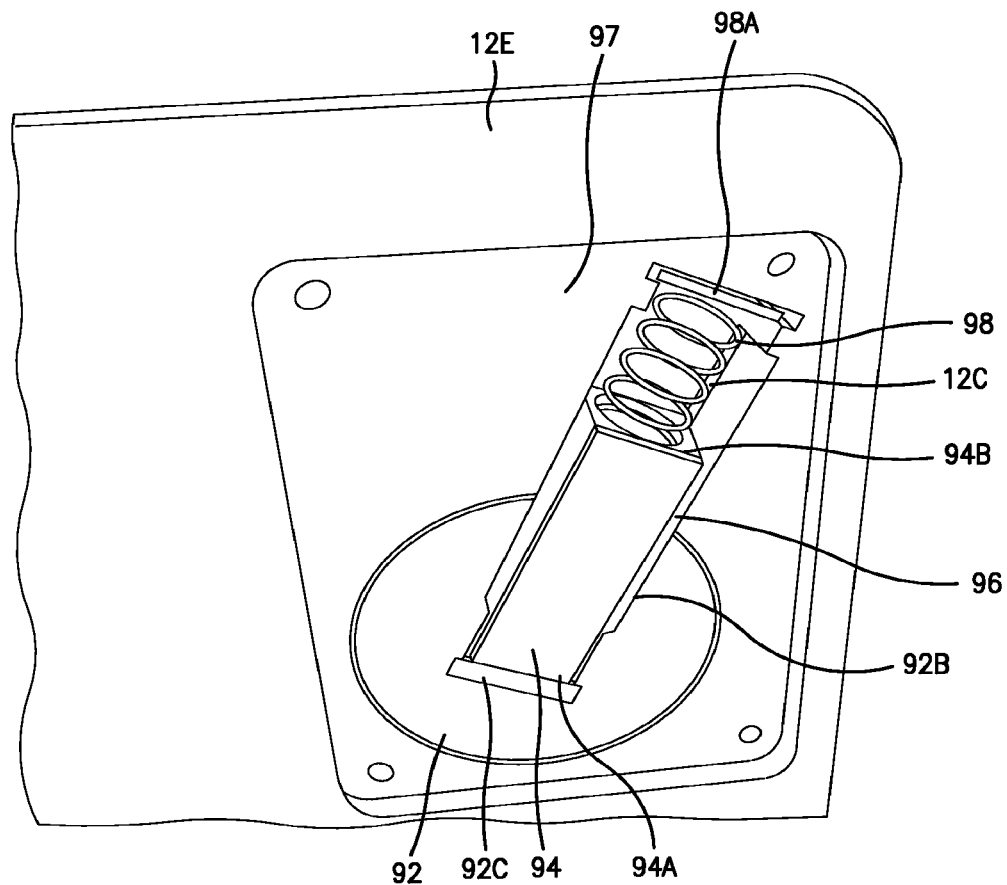
Figure 23:
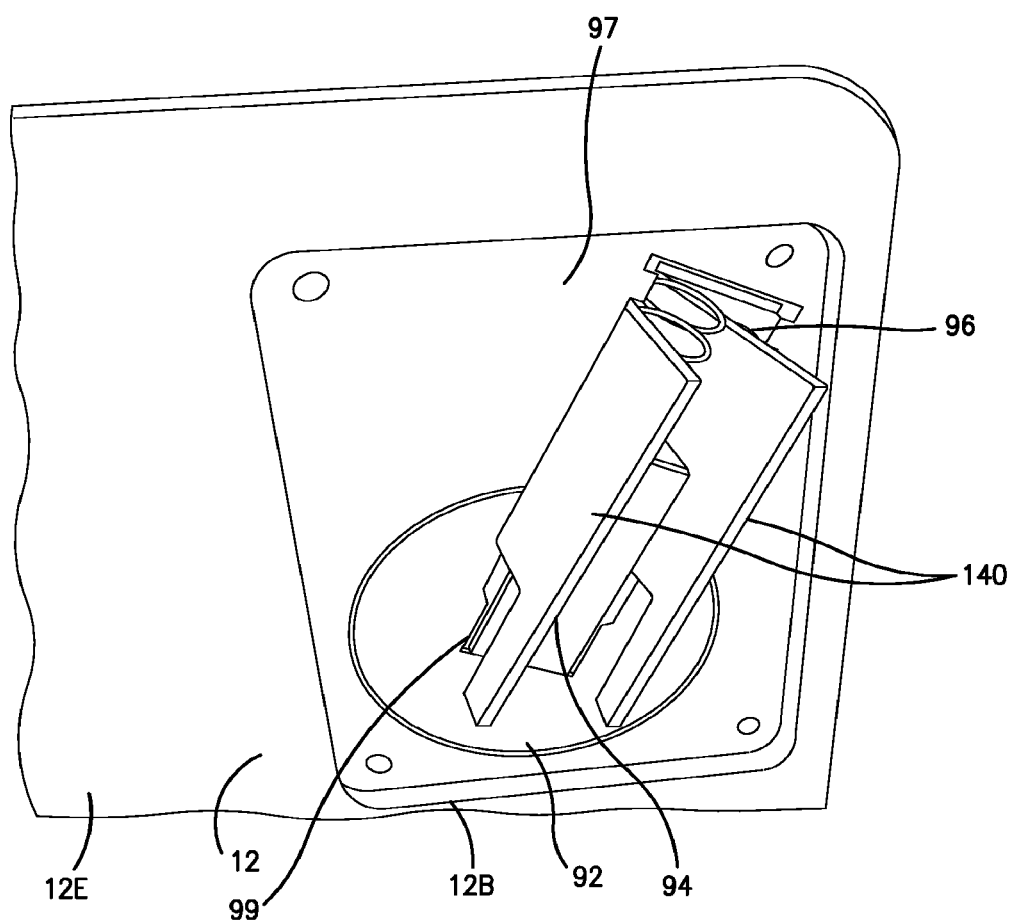

The base 12B of the gauge housing 12 can include a base track segment 12C. The base track segment 12C and the shield track segment 92B can be aligned to form the track 96. The sliding block 94 can be placed in the track 96 formed by the base track segment 12C and the shield track segment 92B. In the first position of the sliding block 94, the sliding block 94 extends through the shield track segment 92B such that an end 94A of the sliding block abuts against an interior wall 92C of the safety shield 92 as shown in FIG. 22. The portion of the interior wall 92C that the sliding block 94 abuts can comprise a hardened material, such as hardened steel, as will be explained in more detail below. In this first position the vertical cavity 14 and the vertical conduit 32 which it partially forms are closed by the sliding block 94. In the second position of the sliding block 94, the end 94A of the sliding block 94 is moved away from the interior wall 92C of the safety shield 92 so that the vertical cavity 14 and the vertical conduit 32 which it partially forms are opened so that the source rod 20 can emerge. In such a position, the sliding block 94 is adjacent the vertical cavity 14.

A spring 98 can engage the sliding block 94 to bias the sliding block 94 into the first position. The spring 98 can engage the end 94B of the sliding block 94. Further, base 12 can include a spring guide 98A. The spring 98 can reside between the spring guide 98A and the end 94B of the sliding block 94.

As shown in FIG. 2, the safety shield 90 and sliding block 94 of the radiation shield assembly 90 are operatively positioned to minimize the user's exposure to radiation when the radiation source 22 is in the safe position. The safety shield 90 can be constructed of lead or tungsten. However, other radiation shielding material may be used. The sliding block 94 can also comprise radiation shielding material such as tungsten.

The gauge 10 can include a remote user interface that can be used to initiate a measurement of the gauge 10 in addition to the user interface 13 on the gauge housing 12. For example, the remote user interface can be a remote keypad 120 as shown in FIGS. 1-3 and 25B. The remote keypad 120 can be located on a top of the tower 30 and distal from the gauge housing 12. The remote keypad 120 can comprise multiple switch states. The states can include a start switch 122 and an escape switch 124. The start switch 122 can be used to begin a gauge count or other tests once the gauge 10 and source rod 20 are in a proper position. The escape switch 124 can be used to abort such tests. The tower 30 can include a routing compartment 39 for routing the electrical wiring for the second keypad 120 into the gauge housing 12 for connection with the CPU 17. The routing compartment 39 can be a separate channel or a passageway within the tower 30. Alternatively, the remote keypad can be a wireless control mechanism, such as a fob, which is physically separated from the gauge 10 and is in wireless communication with the gauge 10.

Figure 26:
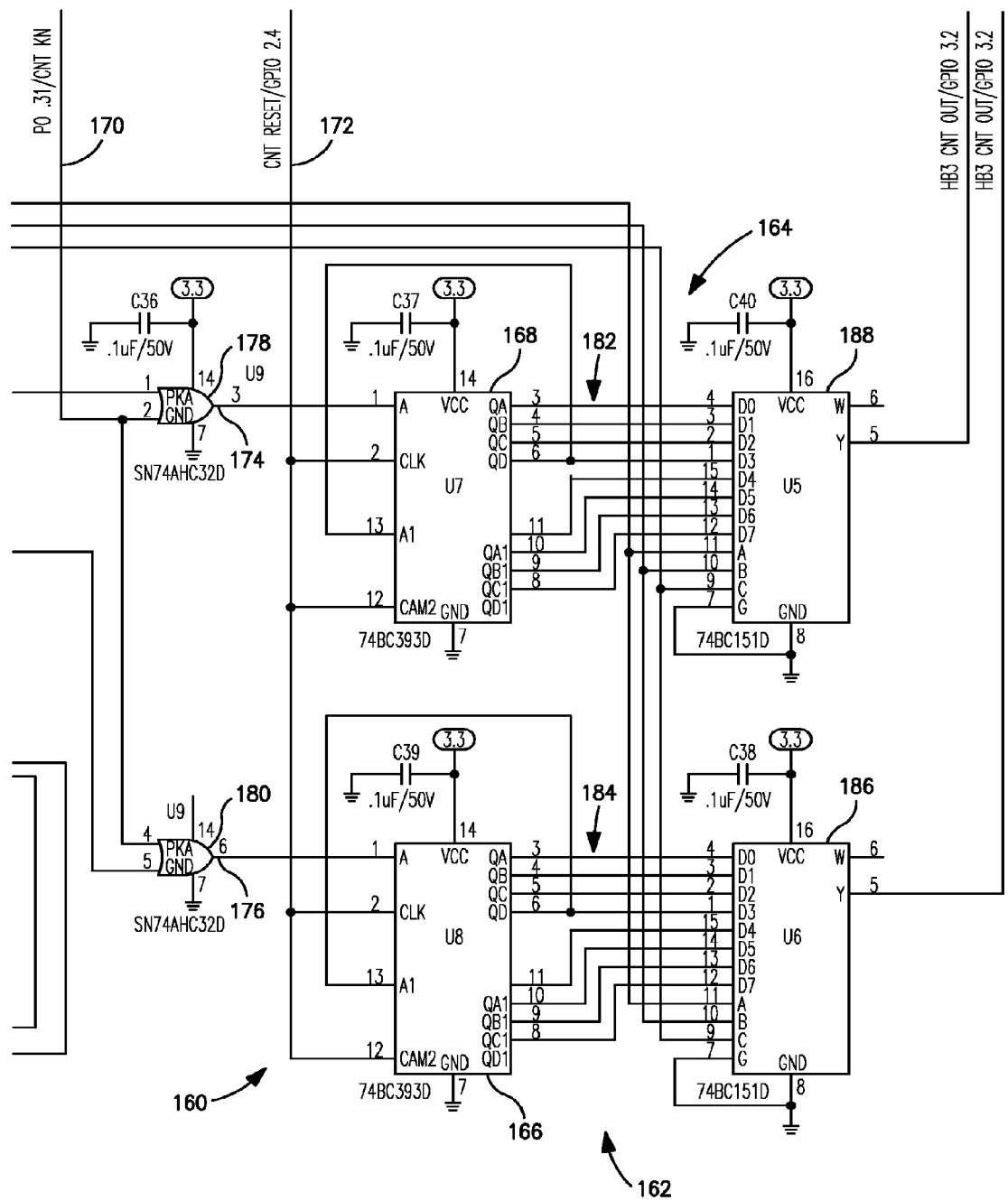
FIG. 26 illustrates a schematic view of an embodiment of a circuit that can be used in a nuclear gauge according to the present subject matter.
Figure 27:
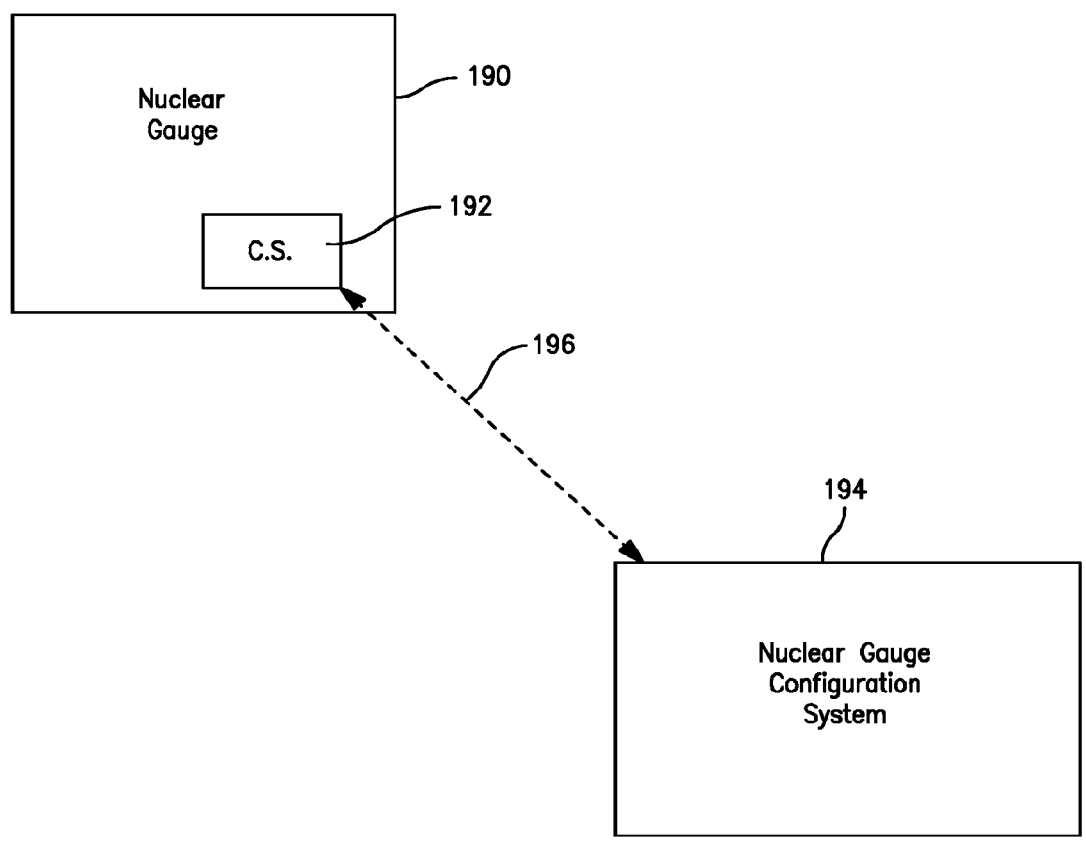
FIG. 27 illustrates a schematic view of an embodiment of a nuclear gauge in communication with a nuclear gauge configuration system according to the present subject matter.

The gauge 10 can include counting circuitry that is used to count pulses. For example, the gauge 10 can have a pulse counting circuit package 160 as shown in FIG. 26. The circuit package 160 can include multiple identical counting circuits such as 162 and 164. The circuit 162 is for the density measurement and the circuit 164 for the moisture measurement. Each circuit 162, 164 can include a 4-bit binary ripple counter 166, 168 so that the circuit package 160 has dual 4-bit binary ripple counters 166, 168. The counters 166, 168 can be designed to count to eight bits (255) by connecting the output of one 4-bit counter to the clock input of the other counter in the package 160. In one embodiment, every negative transition on the input A will cause the counter to increment by one. Exemplary sensors for the density circuit can be GM, proportional, avalanche, solid state, and scintillation detectors. Sensors for the moisture circuit can be $He^3$ proportional, or even electromagnetic in nature.

The counters 166, 168 are reset and enabled by two control lines from the CPU 17: an enabling control line 170 (CNT_EN) and a reset control line 172 (CNT_RESET). When control line 170 carries a high signal (CNT_EN), the counters 166, 168 are disabled. This sets an output from an OR gate 178 on line 174 to high and an output of an OR gate 180 on line 176 to high and disables the G-M and He$^3$ pulses. The counters 166, 168 are then reset to zero when the signal (CNT_RESET) from reset control line 172 is high. The signals (CNT_EN) and (CNT_RESET) are logic 1 to reset the counter 166, 168 to zero and disable counting. When the signal (CNT_RESET) from reset control line 172 and the signal (CNT_EN) from control line 170 CNT_ENABLE are low, the counters 166, 168 will count pulses from, for example, the G-M and He$^3$ tubes.

Since the counters' maximum count is 255, the microcontroller on the CPU 17 regularly reads the counter outputs QA, QB, QC, QD, QA1, QB1, QC1, and QD1 from lines 182 and lines 184 to look for overflow. When the counter output QA, QB, QC, QD, QA1, QB1, QC1, QD1 changes from low to high and back to low, the software increments its internal counter by 256. For example, the counter output QA can transition from low to high and back to low every two counts, the counter output QB can transition from low to high and back to low every four counts, and so on. When the count time is finished, the CPU 17 reads the lower order bits from each counter. Also, when the count time stops, the CPU 17 will set signal (CNT_EN) high.

The CPU 17 can only read one output from the counters 166, 168 at a time. Circuit 162 includes an 8-to-1 multiplexer 186 and circuit 164 includes an 8-to-1 multiplexer 188. Each 8-to-1 multiplexer 186, 188 is used to select which counter output the CPU 17 will read. Three control lines from the CPU 17 (SELA, SELB, and SELC) make the selection. The control lines (SELA, SELB, and SELC) are high as the CPU 17 monitors the output QD1 for overflow. During the counting time, the counter output can be monitored and SELA, SELB, and SELC all equal to 1. At the end of a count, the signal (CNT_EN) from control line 170 goes low to disable counting, and then the selection lines increment from binary 000 to binary 111, while the CPU 17 reads each output line.

A primary function of the gauge 10 is to collect and store information in user created projects. This project information is kept in electronic memory in the CPU 17 in the gauge 10. This information can be transferred to a computer, such as a personal computer using a serial cable connection between the personal computer's com port and the gauge's com port. Then, the data is transmitted from the gauge 10 to the personal computer. This process means that the user must bring the gauge 10 close to the personal computer (within the serial cable length), start a data transfer program (mainly using a terminal emulation program), and instruct the gauge 10 to transfer the data.

Alternatively, a portable storage device can be used to transfer the data. Some embodiments of gauge 10 can use USB based mass storage devices to transfer this information. A USB hosting device that supports a USB mass storage device interface can be used inside the gauge 10. The hosting device has a USB port as shown in FIG. 1 and a serial port (not shown). The gauge 10 can communicate with the hosting device over the serial port, and the hosting device controls a USB mass storage device placed in the USB port. Project information can be sent to the USB mass storage device while it is in the USB port 19 on the gauge 10. Then the USB mass storage device can be removed. It can then be taken to a computer such as a personal computer and plugged into the personal computer's USB port. The user can then move the project information from the USB mass storage device to the PC's internal memory for further uses like creating reports, printing the project, or importing the data into a spread-sheet.

The gauge 10 can include a global positioning system (GPS) receiver 17B as shown in FIG. 2 that is in communication with the CPU 17. The GPS receiver 17B can be used to update the clock/calendar in a gauge 10. A GPS receiver 17B can receive time information from satellites. This information can be set relative to the time at 0 degrees longitude (GMT). If the gauge users set the hour offset for their local time zone with respect to GMT time, the gauge can keep its clock/calendar corrected whenever a GPS signal is received. The gauge simply adds the offset to the GPS supplied time, checks the gauge's clock/calendar, and corrects the reading if needed. An additional method to achieve automatic time/date updates can be to have antennae circuitry that is configured to receive 60 kHz VLF radio time signals transmitted by NIST from station WWVB near the US atomic clock in Boulder, Colo. This same technology is used to update so called "atomic clocks".

The gauge 10 can have the capability to ask the users what time zone offset they would like (up to +/− 12 hours), and store that offset in non-volatile memory. With the integration of a GPS receiver 17B in a moisture density gauge 10, the time and/or date can be automatically updated from the data acquired from the GPS receiver 17B. Depending on the NEMA mode of the GPS receiver 17B, every reading can contain a time/date stamp accurate to within nanoseconds.

The use of the GPS receiver 17B can also be used to improve the quality of readings taken by the gauge 10. A practice of some moisture density gauge operators is to find a "good" or acceptable measurement location and to take consecutive readings claiming these readings were acquired at multiple locations on an asphalt mat. Because the time function on a moisture density gauge is currently adjustable by the operator, the actual reading time record can be altered before making a measurement. If the time/date adjustment is unavailable to the gauge operator and is instead automatically managed by collecting the information from the GPS receiver 17B, every reading stored in memory could have an accurate time/date stamp. In addition, the time/date information can be associated with the location information thus making it impossible to "fudge" or manipulate the data collected. In this manner, the quality of the readings taken by the gauge 10 can be improved by reducing the opportunity for erroneous measurement locations to be reported.

An embodiment of the tower 30, handle 50, radiation shield assembly 90 and other related features will now be described in more detail. The tower, or source rod housing, 30 as shown in FIGS. 1-8 provides sturdiness and durability to protect the source rod 20. The tower 30 can substantially surround the source rod 20. The tower 30 provides a structure that supports the source rod 20 and limits the amount of stress placed on the source rod 20 that can occur by an unintended clockwise or counterclockwise torque. Such torque can occur when the source rod 20 is in a safe position. Thereby, the tower 30 provides a stiffer source rod 20 positioning as compared to gauges without a tower. The tower 30 can have any cross-sectional shape. For example, the tower 30 may have a cross-section that is circular, square, rectangular or the like. Further, as shown in the Figures, the tower 30 can have a triangular cross-section. The tower 30 can comprise a metal or a hardened plastic. For example, the tower 30 can be extruded aluminum.

Figure 4A:
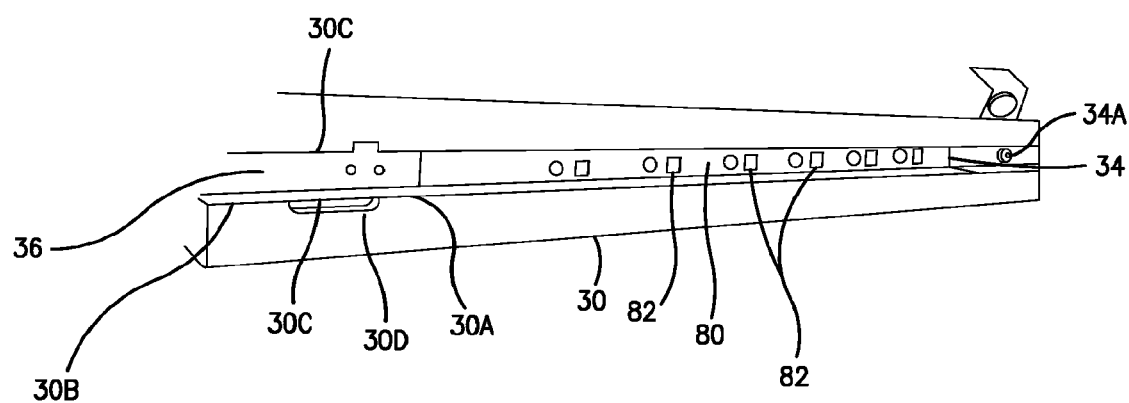
FIG. 4A illustrates a perspective view of an embodiment of a support tower, or source rod housing, used in a nuclear gauge according to the present subject matter.
Figure 4B:
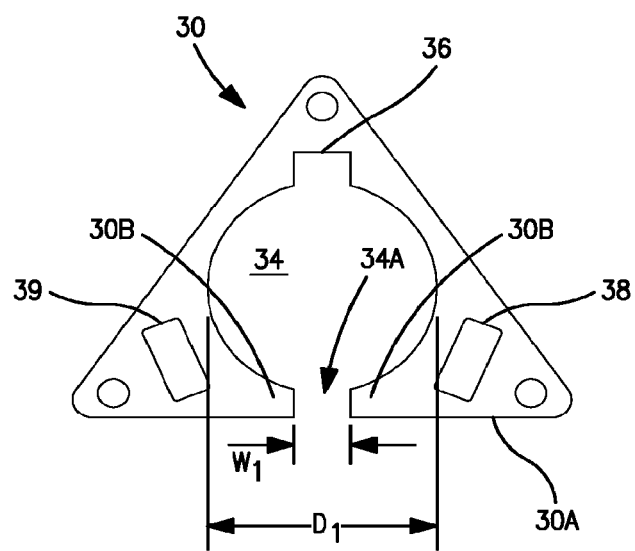
FIG. 4B illustrates a horizontal cross-sectional view of the support tower illustrated in FIG. 4A.

The channel 34 in tower 30 is wide enough to provide sufficient clearance for the source rod. For example, as shown in FIG. 4B, the channel 34 can have a circular cross-sectional diameter $D_1$ that provides easy movement of the source rod 20 therein. The channel 34 can have an inlet 34A that is formed by edges 30B and opens to a side 30A of the tower 30. The handle 50 affixed to the source rod 20 can be configured to slidably engage the inlet 34A. Handle 50 can have a grip portion 50A that extends outward from the tower 30, an engagement portion 50B that is adjustably connected the source rod 20 and a neck portion 50C that is disposed between the grip portion 50A and the engagement portion 50B. The inlet 34A can have a width $W_1$ in which the neck portion 50C can reside. The width $W_1$ of inlet 34A can be less than the diameter or width of the source rod 20.

Figure 13A:
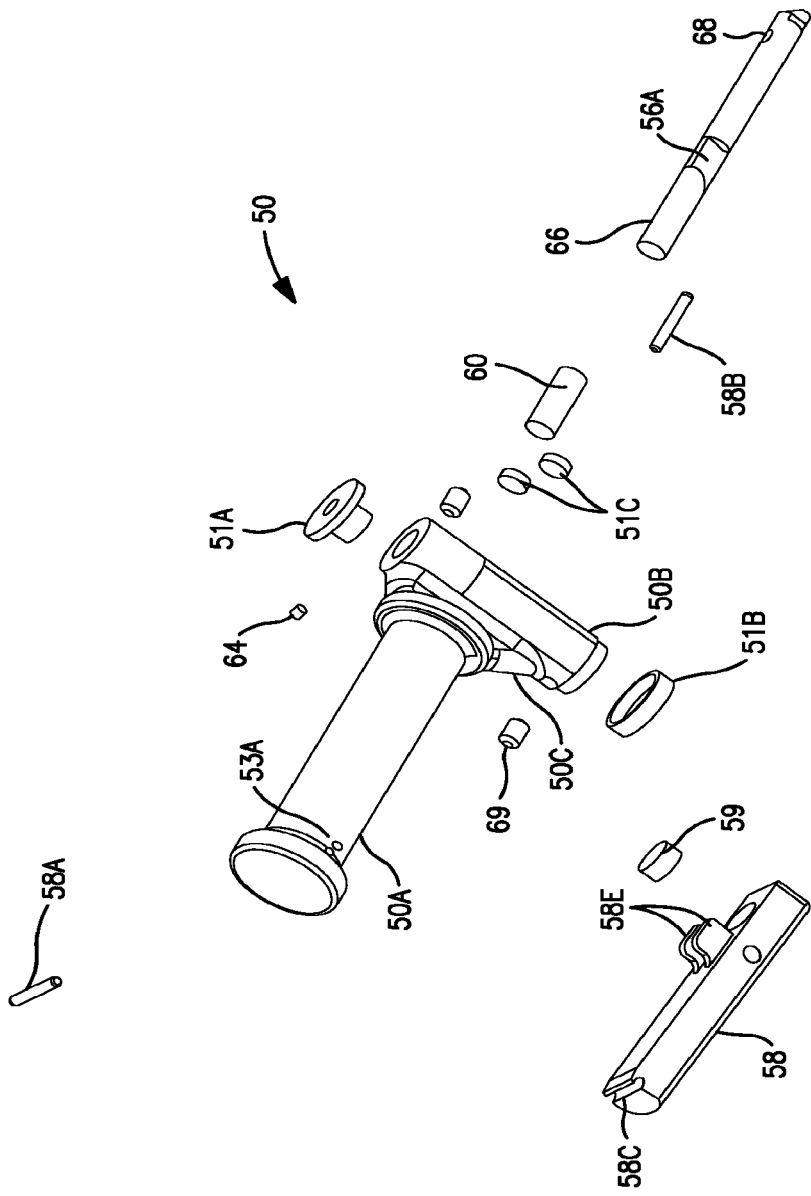
FIGS. 13A-13C illustrate exploded views of an embodiment of a handle used in a nuclear gauge according to the present subject matter.
Figure 13D:
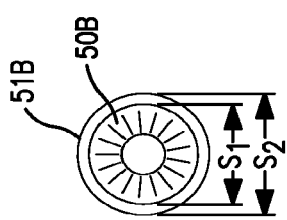
FIG. 13D illustrates horizontal cross-sectional view of the handle illustrated in FIG. 13A.
Figure 13B:
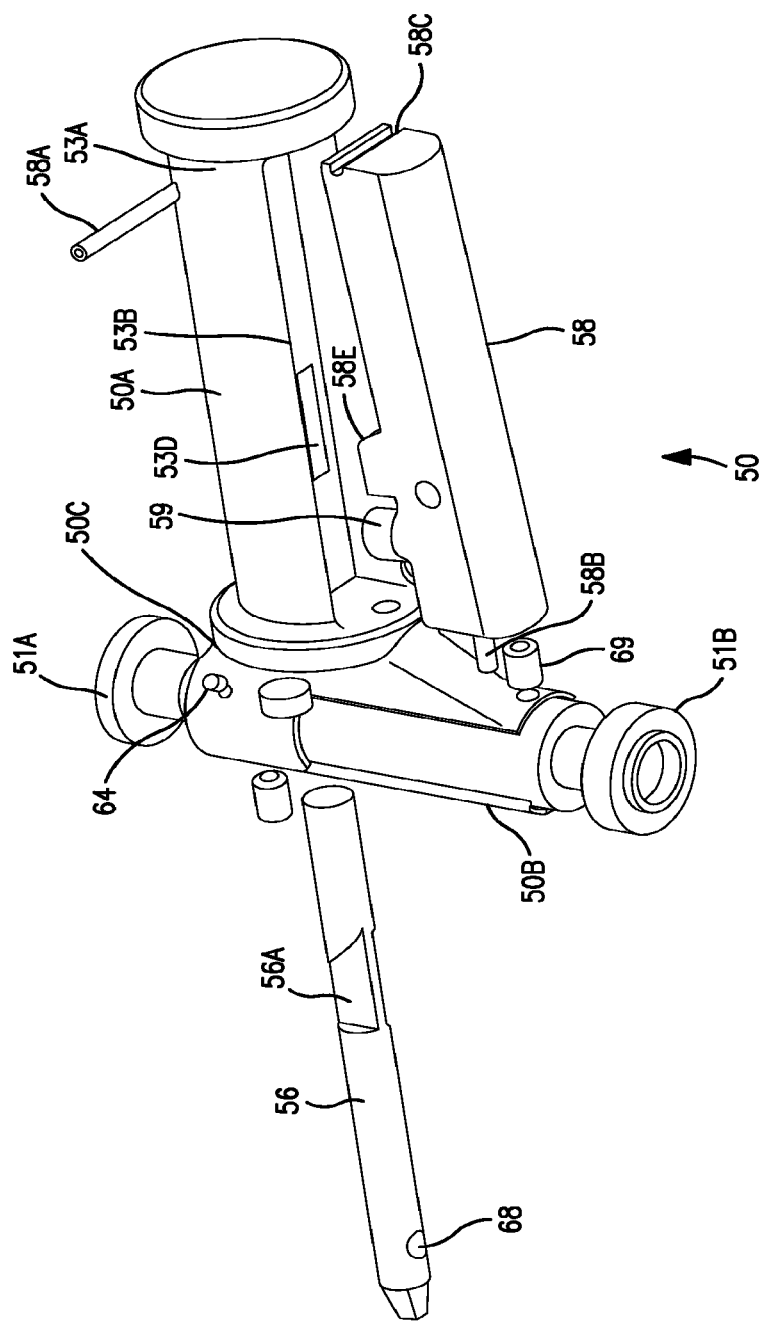
Figure 13C:
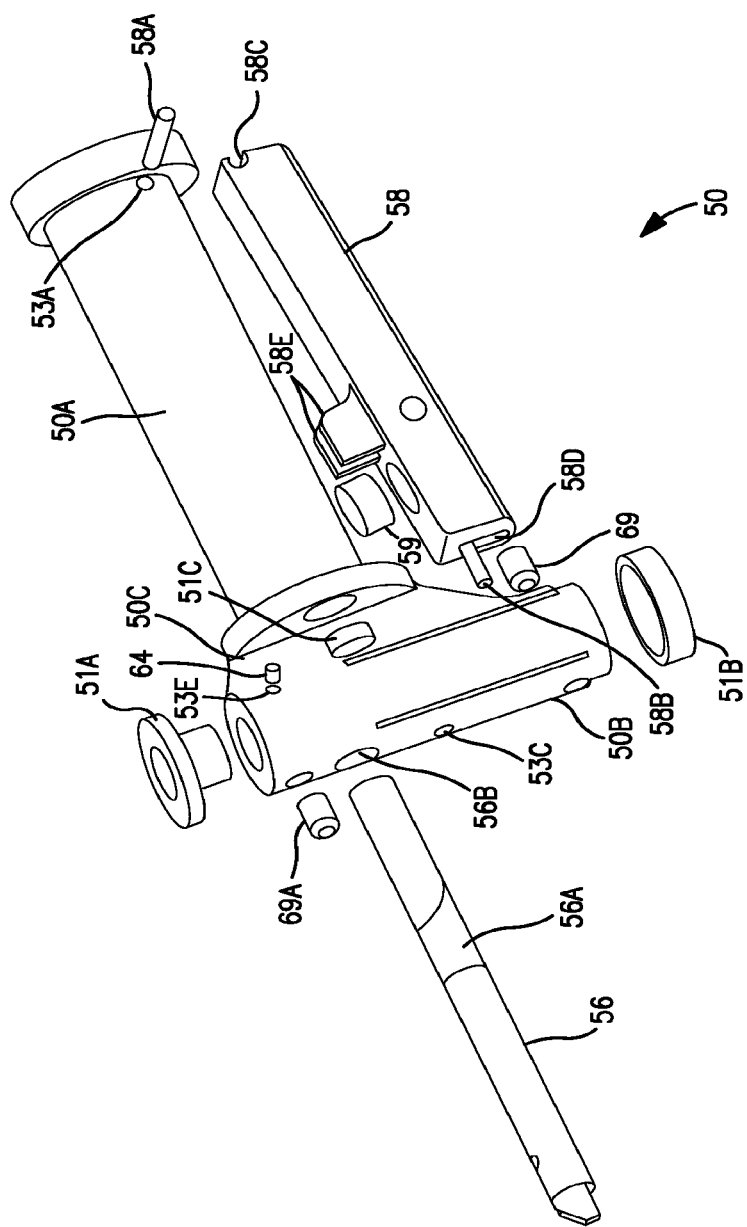

The engagement portion 50B can be configured to slidably engage the channel 34. For example, the handle 50 can include slider pads 51C and/or at least one slider disc as shown in FIG. 13C. In the embodiment shown in FIGS. 13A-13D, a top slider disc 51A and a bottom slider disc 51B are provided that are positioned on either end of the engagement portion 50B of the handle 50. The slider discs 51A, 51B can have a cross-sectional shape taken in a plane parallel to the grip portion 50A of the slider discs 51A, 51B that is larger than the cross-sectional shape of the engagement portion 50B. For example, the cross-sectional view of the engagement portion 50B below the grip portion 50A and the neck portion 50C illustrated in FIG. 13D shows the outer diameter $S_2$ of the of the bottom slider disc 51A being larger than the outer diameter $S_1$ of the engagement portion 50B. The cross-sectional shapes of the top and bottom slider discs 51A, 51B can be approximately the same size. For example, the outer diameters of the top and bottom slider discs 51A, 51B can be equal. The outer diameters of the top and bottom slider discs 51A, 51B can be similar in size to the diameter $D_1$ of the vertical channel 34 of the tower 30. Thereby, the slider discs 51A, 51B can enhance the stability of the source rod 20 in the vertical channel 34 of the tower 30 and can assist in reducing radial movement of the source rod 20 at the end engaged by the handle 50.

The slider discs 51A, 51B can be at least partially formed from a friction reducing material. For instance, the slider discs 51A, 51B can have an outer perimeter that interfaces with the tower 30 in the vertical channel 34 that is a friction reducing material. For example, the slider discs 51A, 51B can be or can include a polymer having a low coefficient of friction. The polymer can be at least one of polytetrafluoroethylene, perfluoroalkoxy, and fluorinated ethylene propylene.

The handle 50 can include a plunger 56 and a trigger 58. The plunger 56 can be extendable to engage index holes 82 of the index positioning strip 80 disposed within the tower 30 and retractable to disengage the index holes 82 by actuation of the trigger 58. The trigger 58 can be located on the underside of the grip portion 50A of the handle 50. The trigger 58 can be held in place by a pair of pins 58A, 58B. The end of the trigger 58 distal from the neck portion 50C of the handle 50 can have a pivot groove 58C that engages pivot pin 58A to create a pivot point for the trigger 58. The pivot pin 58A can reside in the pivot aperture 53A defined in the grip portion 50A. The trigger 58 can include a vertical extending slot 58D as shown in FIGS. 2 and 13C that can engage locking pin 58B. The slot 58D permits the trigger 58 to be moved up and down with the pin 58B residing in the slot 58D. A trigger spring 59 can engage the trigger 58 at a position on the trigger closer to the slot 58D and more distal from the groove 58C. The trigger spring 59 biases the trigger 58 away from the plunger 56. The handle 50 can also include a spring 60 that engages the plunger 56 and a spring guide 62 within the grip portion 50A. The spring 60 biases the plunger 56 towards an extended position.

The trigger 58 can include at least one protrusion 58E that engages at least one retraction groove 56A on the plunger 56. In the embodiment shown, two protrusions 58E are provided on the trigger 58 and two retraction grooves 56A are provided on the plunger 56. However, it is understood that one or more protrusions and corresponding retraction grooves may be provided.

The protrusions 58E can be slanted to match a slant in the groove 56A. The slant of the protrusions 58E and the retraction grooves 56A are such that, as the trigger 58 is squeezed upward, the protrusions 58E engage the retraction grooves 56A forcing the plunger 56 to a retracted position. Once the source rod is moved to one of the predetermined source rod locations that is aligned with a corresponding index hole 82, the trigger 58 can be released. The trigger spring 59 biases the trigger 58 away from the plunger 56 and the spring 60 biases the plunger 56 towards an extended position with the plunger 56 engaging the corresponding index hole 82.

Figure 5:
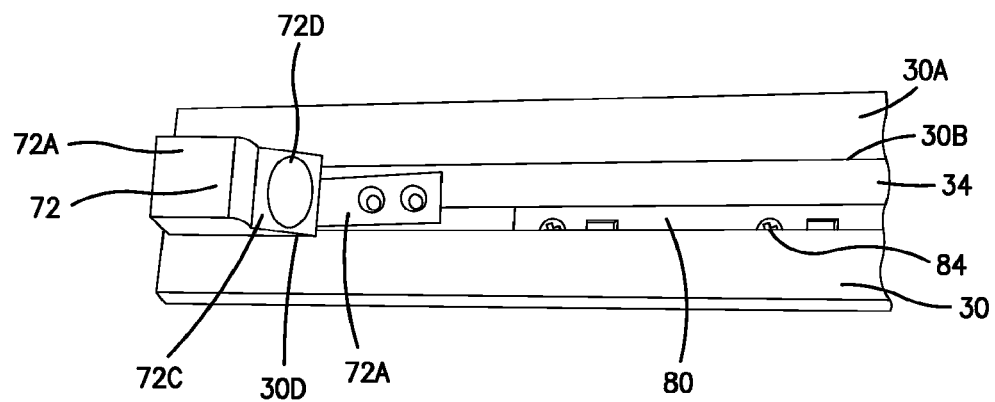
FIG. 5 illustrates a close-up perspective view of the support tower illustrated in FIG. 4A.
Figure 6:
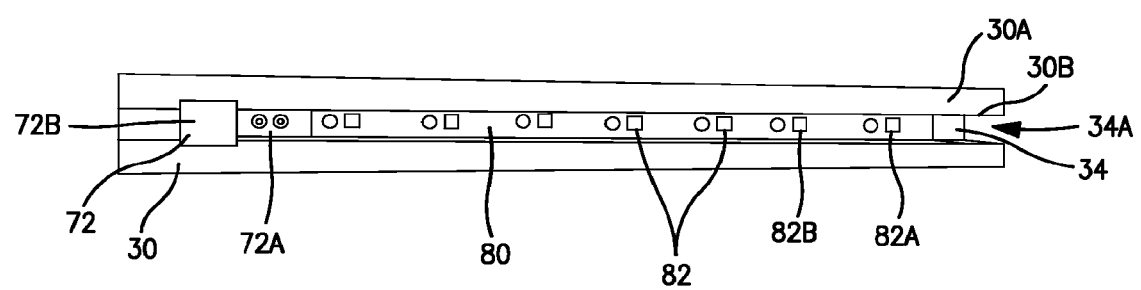
FIG. 6 illustrates a perspective view of the support tower illustrated in FIG. 4A.
Figure 7A:
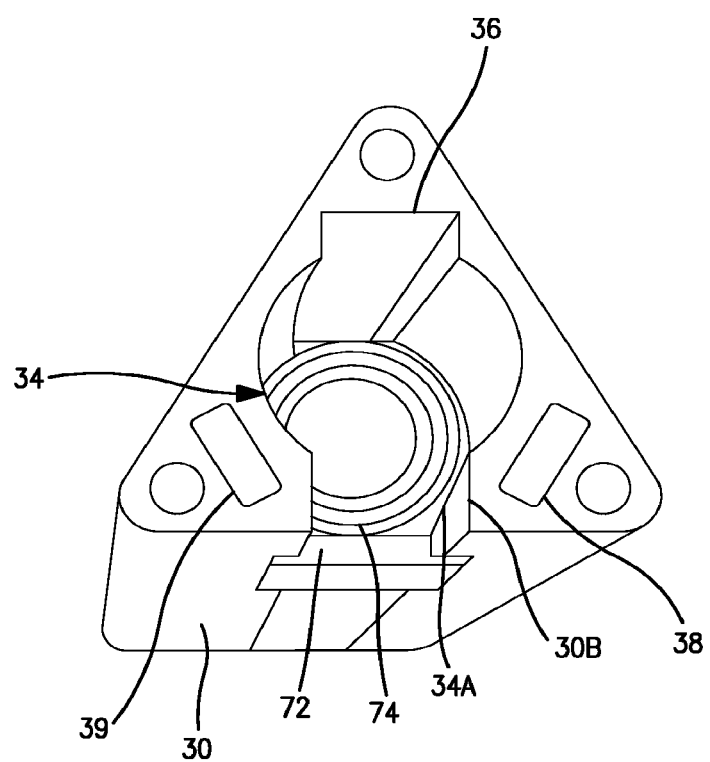
FIG. 7A illustrates a perspective end view of the support tower illustrated in FIG. 4A.
Figure 7B:
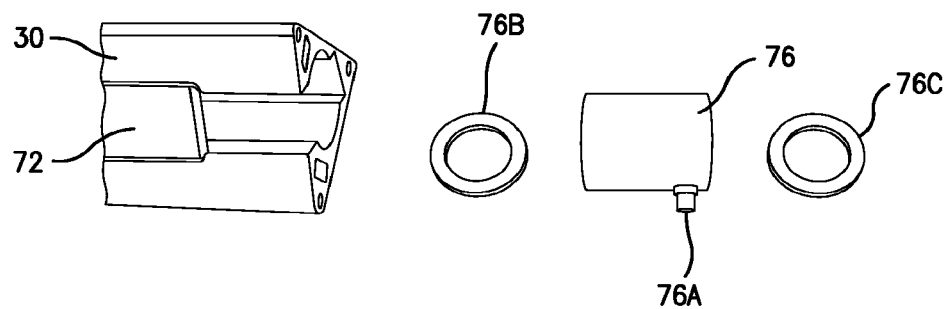
FIG. 7B illustrates a perspective view of the support tower illustrated in FIG. 4A and an embodiment of a tube spacer to be inserted into the tower according to the present subject matter.
Figure 7C:
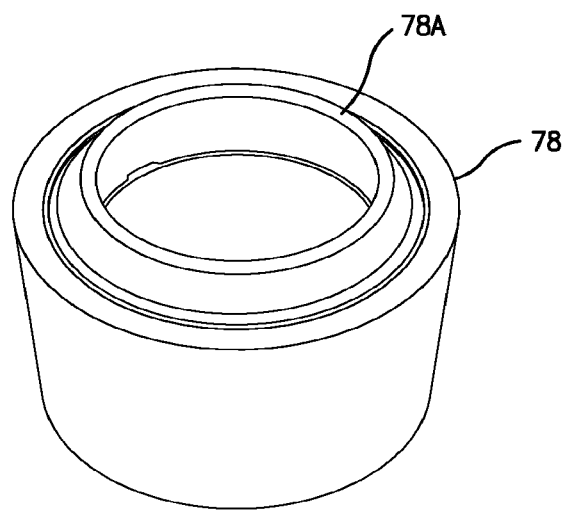
FIG. 7C illustrates a perspective view of an embodiment of a source rod bearing to be inserted into a support tower, or source rod housing, according to the present subject matter.
Figure 8:
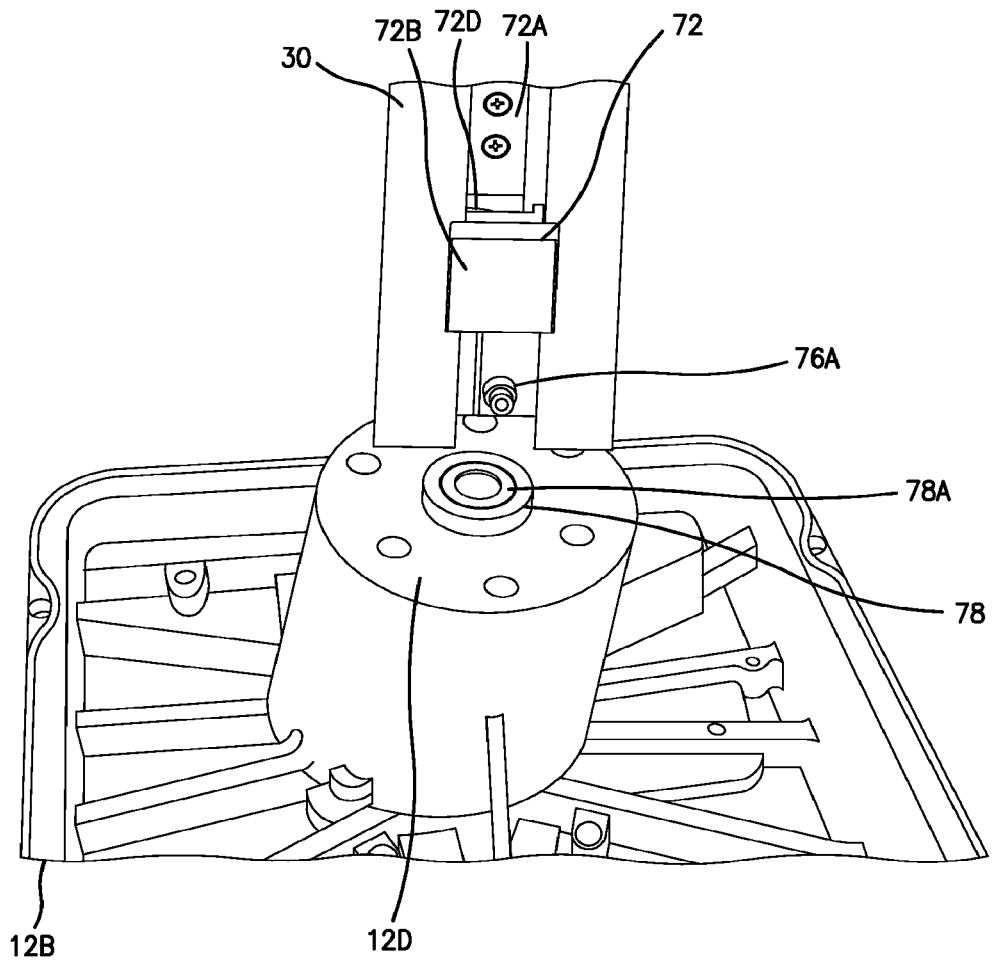
FIG. 8 illustrates a perspective view of an embodiment of a support tower, or source rod housing, and base of a gauge housing according to the present subject matter.

The index holes 82 of the index positioning strip 80 can provide different source rod locations by holding the source rod 20 at different positions as shown in FIGS. 2-6. These locations can include, for example, index hole 82A as shown in FIG. 6 that corresponds to the "safe" position wherein the radiation source 22 is raised and shielded from the test material. The safe position is used to determine the standard count. Another index hole 82B corresponds to the backscatter mode wherein the radiation source 22 is located adjacent to the surface of the test material underlying the gauge 10. Other index holes 82 can correspond to a plurality of direct transmission positions. The use of the index positioning strip 80 with its adjustability permits less stringent manufacturing tolerances. Therefore, the index positioning strips 80 allow greater variability with this design. Thus, the position of the strip 80 can be adjusted for additional manufacturing flexibility. The strip 80 can be attached in different manners. For example, the tower 30 can include adjustment screw holes 36A (see FIG. 2) that can align with apertures 84 in strip 80 for insertion of screws. Thus, adjustment screw holes 36A and apertures 84 can be used to secure the strip 80 to the tower 30. The index positioning strip 80 can be convertible to a length that can be used with a 12-inch source rod, an 8-inch, or to a length that is usable with a backscatter only gauge.

The safe position corresponding to the index holes 82A can position the tip of the source rod 20 at least about 2.20 inches above the outer surface of the base 12B of the gauge housing 12. This places the radiation source 22 in a position that exhibits reduced sensitivity of the standard count to slight radiation source positioning variability in the vertical direction. Specifically, the radiation standard count rate with the radiation source 22 in the safe position changes only about 2-10 scaled counts per mil of radiation source position change in the vertical direction in the gauge 10.

Figure 9:
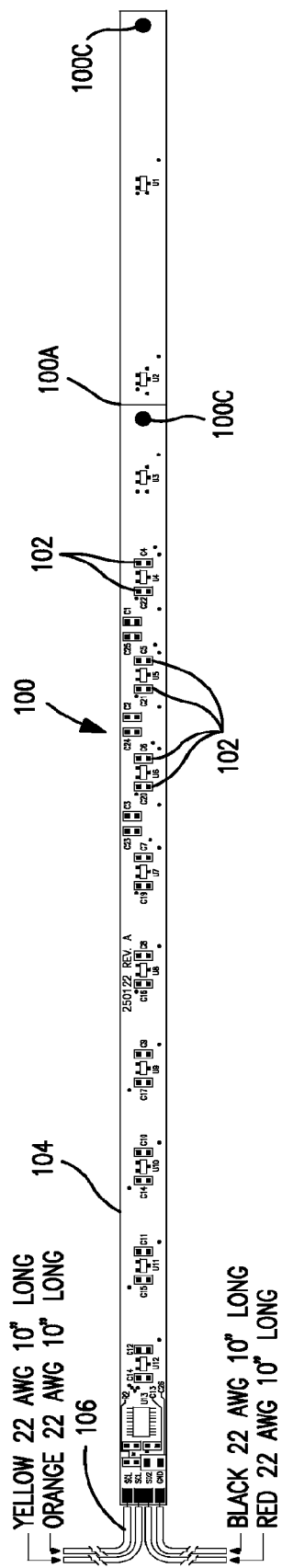
FIG. 9 illustrates a plan view of an embodiment of a depth strip that can provide a non-contact measurement in a nuclear gauge according to the present subject matter.
Figure 10:
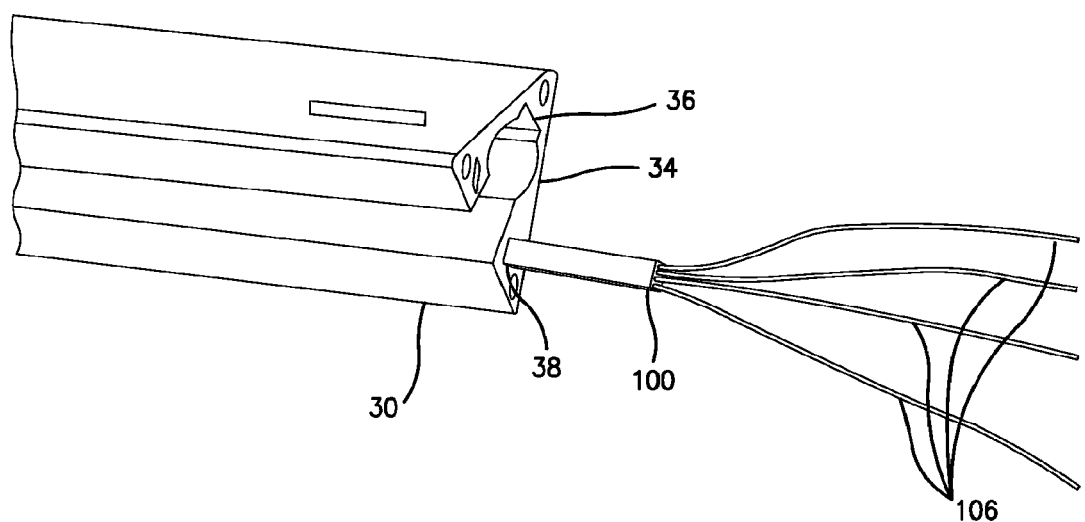
FIG. 10 illustrates a perspective view of an embodiment of a support tower, or source rod housing, and depth strip according to the present subject matter.
Figure 11:
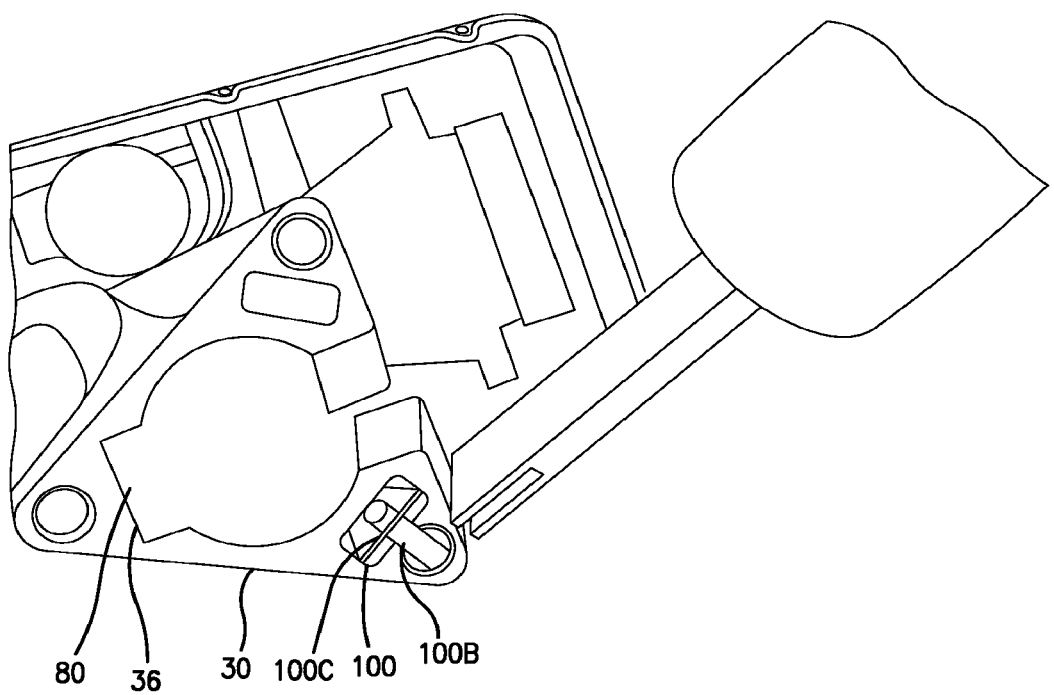
FIG. 11 illustrates a perspective end view of the support tower and depth strip illustrated in FIG. 10.

As illustrated in FIGS. 9-11, a depth strip 100 can be positioned in the tower 50 and can provide non-contact measurements used to determine the depth at which the source rod 20 is positioned during use. For example, the tower 50 can include a measurement compartment 38 in which the depth strip 100 can be placed. The measurement compartment 38 can be a channel or groove. Alternatively, the compartment 38 can be a passageway within the tower 30 in proximity to the vertical channel 34 in which the source rod 20 resides. As stated above, the depth strip can use optical sensors, such as optical range finder sensors, acoustic sensors, magnetic sensors and the like to provide non-contact measuring of the positioning of the source rod.

As described above, the depth strip 100 that resides in the measurement compartment 38 can be a sensor that uses magnetically actuated, low power Hall Effect sensors 102 as the means to determine the rod position. For example, the Hall Effect sensors 102 of the depth strip 100 can be alignable with the index holes 82 of the index positioning strip 80. The Hall Effect sensors 102 can be mounted on a source rod position detection circuitry, such as a printed circuit board, 104 at discrete positions which are spaced about one inch and/or about two inches apart. The printed circuit board 104 can include other electronics to power the Hall Effect sensors 102, determine which Hall Effect sensor 102 is activated, and communicate this information with the gauge CPU 17 that is in communication with the user interface 13. This configuration allows for absolute location of the source rod, not just relative to the safe position.

The handle 50 can include a magnet 64 thereon that is detectable by the Hall Effect sensors 102 to provide non-contact measuring of the positioning of the source rod 20. The Hall Effect sensors 102 can be placed on the printed circuit board 104 so that they will line up with the magnet 64 located on the handle 50 of the moveable source rod 20. The source rod 20 can be then "indexed", such that it can only be placed in discrete positions through the use of the index positioning strip 80. These positions can be about one inch or about two inches apart. Special indexing is also achievable by replacing the strip. At each of these discrete positions, the magnet 64 in the handle 50 can be positioned directly across from one of the Hall Effect sensors 102 on the printed circuit board 104. Thus, only one of the Hall Effect sensors 102 is actuated at a time. When the user starts a gauge operation that is source rod position sensitive, the CPU 17 can communicate with the printed circuit board 104 electronics to determine which Hall Effect sensor 102 is activated. The CPU 17 software can be structured such that it can relate the actuated Hall Effect sensor 102 to a known index position. If a Hall Effect sensor 102 is not actuated, the CPU 17 can inform the gauge user that the source rod 20 is not in a valid position. If a Hall Effect sensor 102 is actuated, the CPU 17 can start the gauge operation, and pass the index position to the software. In this manner, the gauge user does not have to manually enter the source rod position.

By including a parting line 100A along the printed circuit board 104, the depth strip 100 is convertible from a 12-inch unit to an 8-inch unit along the parting line. In this manner, a single designed depth strip 100 can be used in different gauges 10 that have two different distances at which the source rod 20 can extend. For 8-inch units, the depth strip 100 can be parted at this parting line 100A. When not parted, the whole depth strip 100 can be used for 12-inch units. The depth strip 100 can include wiring 106 that can be use to connect it to the CPU 17 and/or power source of the gauge 10.

Figure 12:
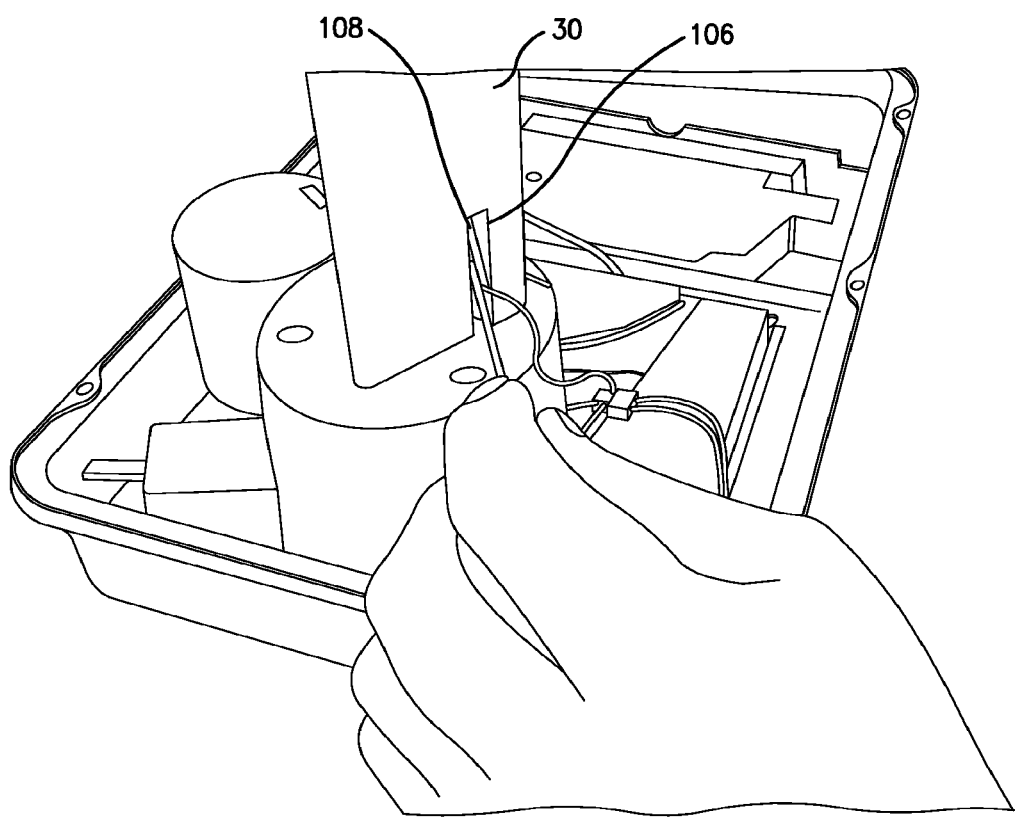
FIG. 12 illustrates a perspective view of an embodiment of a support tower and base of a gauge housing according to the present subject matter.

Before the attachment of the tower 30 to the base 12B of the gauge housing 12, the depth strip 100 can be inserted into the measurement compartment 38 of the tower 30 so that the depth strip is in the proper location to determine the source rod locations based on the position of the indexing holes 82 of the index positioning strip 80. If the compartment 39 is a passageway, the depth strip 100 can be inserted into the measurement compartment at the bottom of the tower 30 so that the top of depth strip 100 extends through the top of the tower 30. A placement pin 100B can be inserted into an aperture 100C in the depth strip 100. After the insertion of the pin 100B, the depth strip 100 can be pushed back into the tower 30 so that the pin 100B engages the top of the tower 30 so that the Hall Effect sensors 102 align with the index holes 82 of the index positioning strip 80. For example, the tower can include a seat that receives the pin 100B. After insertion, the integrated circuits, or Hall Effect sensors, 102 of the printed circuit board 104 of the depth strip 100 should face the vertical channel 34 where the source rod 100 will reside after insertion into the tower 30. The tower 30 can include a wiring aperture 108 through which the wiring 106 can be pulled as shown in FIG. 12. The wiring 106 can then be properly connected to the gauge 10.

To facilitate proper movement of the source rod 20 within the vertical conduit 32 formed by the vertical channel 34 in the tower 30 and the vertical cavity 14 in the gauge housing 12, the guide and sealing system 70 can be provided. The guide and sealing system 70, as shown in FIGS. 1, 2 and 4-8, can work in conjunction with the at least one slider disc on the handle 50, such as slider discs 51A, 51B, to increase stability and minimize radial movement of the source rod 20. The guide and sealing system 70 can include a bracket 72 that can be placed and secured in the vertical channel 34 of the tower.

The bracket 72 can have a first end portion 72A that is configured to lie flat within the groove 36 in the tower 30. The first end 72A portion can be secured below the index positioning strip 80, but aligned with the index positioning strip 80 within the groove 36. The bracket 72 can also have a second end portion 72B that is configured to reside outside of the channel 34 of the tower 30. For example, as shown in FIGS. 4-6, the second end portion 72B can be wider than the width $W_1$ of the inlet 34. The tower 30 can have a groove 30C cut into each of the edges 30B on either side of the inlet 34A of the channel 34. The second end portion 72B can be configured to reside in the grooves 30C. The second end portion 72B can extend substantially parallel to the first end portion 72A of the bracket 72. Between the first end portion 72A and the second end portion 72B, the bracket 72 can include a mid-portion 72C. The mid-portion 72C can be substantially perpendicular to both the first end portion 72A and the second end portion 72B and also about perpendicular to the vertical channel 34 in which the source rod is disposable. The mid-portion 72C includes a bracket aperture 72D through which the source rod can pass. The edges 30B can also include slots 30D through which the bracket 72 including the mid-portion 72 can pass so that when the bracket 72 is secured in the tower 30, the first end portion 72A resides within the groove 36, the second end portion 72B resides within the grooves 30C, and the mid-portion 72B extends through the slots 30D and into the vertical channel 34 so that the bracket aperture 72D aligns with the vertical channel 34 to accept the passage of the source rod 20 therethrough.

The guide and sealing system 70 (see FIG. 2) can also include an upper seal 74 that can be placed into the vertical channel 34 below the bracket 72 so that the upper seal abuts against the underside of the mid-portion 72C of the bracket. The upper seal 74 can have an inner diameter that is less than the diameter of the bracket aperture 72D and is in close tolerance of the source rod 20. The outer diameter of the upper seal 74 can be substantially similar to the diameter $D_1$ of the vertical channel 34. After the upper seal 74 is seated against the bracket 72, a tube spacer 76 with a grease fitting 76A can be seated against the upper seal 74. The guide and sealing system 70 can also include a source bearing 78 that can be secured against the tube spacer 76 at the end distal from the bracket 72 and upper seal 74. The source rod bearing 78 can include a seal wiper 78A that acts as a lower seal. The source rod bearing 78 can be seated in the shield housing 12D of the base 12B above the radiation shield assembly 90. The tube spacer 76 can include a top washer 76B and a bottom washer 76C that can be placed on either end of the tube spacer. For example, top washer 76B can be placed on the end of the tube spacer 76 proximate to the upper seal 74 and the bottom washer 76C can be placed at the end of the tube spacer 76 proximate to the source rod bearing 78. The source rod bearing 78 can be a bushing. The source rod bearing 78 can guide the source rod 20 through cavity 14 in the gauge housing 12 with an extremely close fit to the source rod 20 in order to minimize variability in radiation source positioning. Specifically, the outer diameter of source rod bearing 78 can be about 1.1265 inches +/− about 0.0005 of an inch and the bearing inner diameter can be about 0.6265 of an inch +/− about 0.0005 of an inch. Additionally, the bearing housing diameter can be about 1.1265 inches +/− 0.0005 of an inch. The source rod 20 diameter can be about 0.625 of an inch +/− about 0.001 of an inch. This results in a nominal bearing clearance of about 0.00025 of an inch and a bearing clearance range of press-fit to about 0.001 of an inch. The nominal source rod clearance can be about 0.00175 of an inch and the source rod clearance range can be from about 0.0005 to about 0.0030 of an inch. Thus, the source rod 20 has a total range of radial movement of no more than about 0.0005 of an inch to about 0.0040 of an inch. Since the desired position of the source rod 20 is on the true centerline of the source rod bearing 78, the movement away from true center is actually the radial clearance, which equals one-half of the diametrical clearance. Thus, the maximum movement away from true center of the source rod 20 can be about one-half of 0.0040 of an inch, or 0.0020 of an inch.

It is important to correctly calibrate the height of the source rod 20 to ensure that the source rod 20 will be at the correct depths when the handle engages the index positioning strip 80. To calibrate the gauge 10, the exact source height can be adjusted in real time by the assembly technician using only a wrench or a screwdriver. The screwdriver or wrench can be inserted into a threaded device, such as a screw or bolt 54A that is securely affixed to the source rod 20 such that the screw does not rotate separate from the source rod. Any type of finely pitched thread device can be used. A screw such as a flathead screw, slotted screw, a Phillips head screw, a star screw such as those sold under the name TORX®, a spline drive screw, hex screw, double hex screw or the like, can be used as the fine adjustment element 54. Similarly, an Allen Head screw can be used.

Access is can be permitted to the screwdriver or wrench through the top of the tower 30 and the handle 50. The remote keypad 120 or other top portion is removed. The handle 50 can define at least one adjustment aperture therein to permit access to the fine adjustment element 54. For example, the handle 50 includes adjustment apertures 66 and 68 as shown in FIGS. 2,13B, and 14 in both the engagement portion 50B and the plunger 56, respectively, so that when the source rod 20 is in backscatter position all the adjustment apertures 66 and 68 in the handle 50 are aligned within reach of the assembly technician's screwdriver or wrench. In the embodiments where the handle 50 can include a plunger 56 and a trigger 58, the plunger 56 can define an adjustment aperture 68 that aligns with the adjustment aperture 66 in the handle 50 when the plunger 56 resides in an extended position.

The coarse adjustment mechanism 52 and fine adjustment element 54, as shown in FIGS. 2 and 14, can be used to set the height of the source rod 20 during manufacturing with the settings being permanent or semi-permanent. "Semi-permanent" as used herein means that the height of the source rod 20 cannot be reset without physical manipulation through the use of chemical and/or mechanical tools. The handle 50 can also include one or more set screws 69 for holding and locking the source rod 20 in place after the height of the source rod 20 is adjusted with the coarse adjustment mechanism 52 and the fine adjustment element 54. The source rod 20 can be in a backscatter position when the height of the source rod 20 is adjusted with the coarse adjustment mechanism 52 and the fine adjustment element 54. This ability greatly reduces assembly time, improves locating precision and repeatability.

Within the handle 50, the coarse adjustment mechanism 52 can include a threaded section 52A and the fine adjustment element 54 can include a screw, such as an Allen Head screw 54A. Such an Allen Head screw 54A can be securely affixed to the source rod 20 such that the screw does not rotate separately from the source rod 20.

The coarse adjustment mechanism 52 permits the quick attachment of the source rod 20 into the handle 50. The fine adjustment element 54 uses the threaded section 52A as well, but fine adjustment element 54 permits for very small incremental movement of the source rod 20 through partial rotation of the source rod 20. The fine adjustment element 54 can permit accurate and acute adjustment of the height of the source rod of less than about one hundredth of an inch. For example, the fine adjustment element 54 can permit adjustment of the source rod 20 to plus or minus about 0.005 of an inch. In some embodiments, the fine adjustment element 54 can permit adjustment of the source rod 20 to plus or minus about 0.001 of an inch. Thus, both coarse adjustments and fine adjustments can be made to the source rod height.

Figure 16:
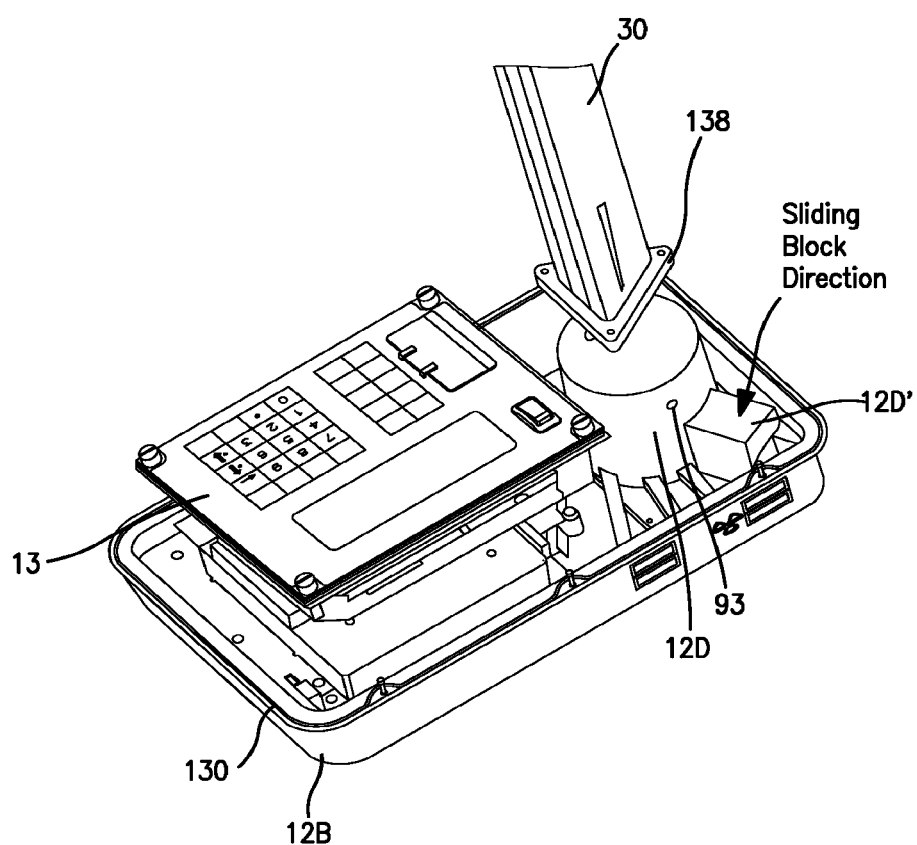
FIG. 16 illustrates a perspective view of an embodiment of a nuclear gauge according to the present subject matter.

In the past, attempts have been made to keep water out of the gauges. Humidity and water can adversely affect the high voltage electronics. The problem has always been to develop a seal that allows the source to move freely up and down while completely blocking humidity and moisture. To protect the electronics contained within the gauge housing 12 of the gauge 10, precautions can be taken to ensure a good seal is created between the top cover 12A and the base 12B of the gauge housing 12 and between the tower 30 and the gauge housing 12. For example, as shown in FIG. 16, an O-ring 130 can be positionable in a groove 132 within the base 12B of the gauge housing 12 between the base 12B and the top cover 12A. The O-ring 130 can extend around an outer parameter of the base 12B with the top cover 12A engaging the O-ring 130 to create water proof seal between the top cover 12A and the base 12B.

Further, as shown in FIGS. 2 and 25A-25C, a second O-ring 134 having a diameter which fits tightly around the cross-section of the tower 30 can be positioned at the tower base where the tower 30 is secured to the gauge housing 12. The use of the O-ring 134 and a trim plate 138 that fit around the horizontal cross-sectional shape of the tower 30 and engage the top cover 12A of the gauge housing 12 allows the entire circumference of the sealing area to be water tight. This can be especially important in gauges that are specified for all weather use. For example, the cross-section of the tower 30 can be triangular in shape and the top cover 12A can form a groove 136 around opening 15 into which tower 30 can extend. A triangular trim plate 138 having an outer edge 139 can push the second O-ring 134 against the tower 30 to create a water resistant seal. The trim plate 138 can be placed around the tower base and over this second O-ring 134 and then secured to the gauge housing 12.

The radiation shield assembly 90 is described below in more detail. As stated above, the radiation shield assembly 90 has a portion that is operatively positionable to move laterally between two positions. A first position is provided for blocking a distal end 14A of the vertical cavity 14 of the gauge housing 12 such that radiation is shielded from exiting the cavity 14. A second position adjacent to the vertical cavity 14 is provided for allowing vertical movement of the source rod 20 through the radiation shield assembly 90. As described above, the radiation shield assembly 90 can include a sliding block 94 positionable to move laterally between the first position and the second position. A track 96 can be configured to receive the sliding block 94 and guide movement of the sliding block 94. A spring 98 can engage the sliding block 94 and bias the sliding block 94 into the first position.

A safety shield 92 can be included in the radiation shield assembly 90. The safety shield 92 can include a shield track segment 92B therein that comprises at least a portion of the track 96. The base 12B of the gauge housing 12 can include a base track segment 12C. The base track segment 12C and the shield track segment 92B are alignable to form the track 96.

At least one replaceable sliding guide 140, as shown in FIGS. 17 and 18A-18C, is positionable within the track 96 adjacent the sliding block 94. The at least one replaceable sliding guide 140 is configured to reduce friction as the sliding block 94 moves between the first position and the second position. The at least one replaceable sliding guide 140 can comprise two replaceable sliding guides 140 with each replaceable sliding guide 140 extending over at least a portion of the base track segment 12C and the shield track segment 92B on opposing walls of the track 96.

Figure 17:
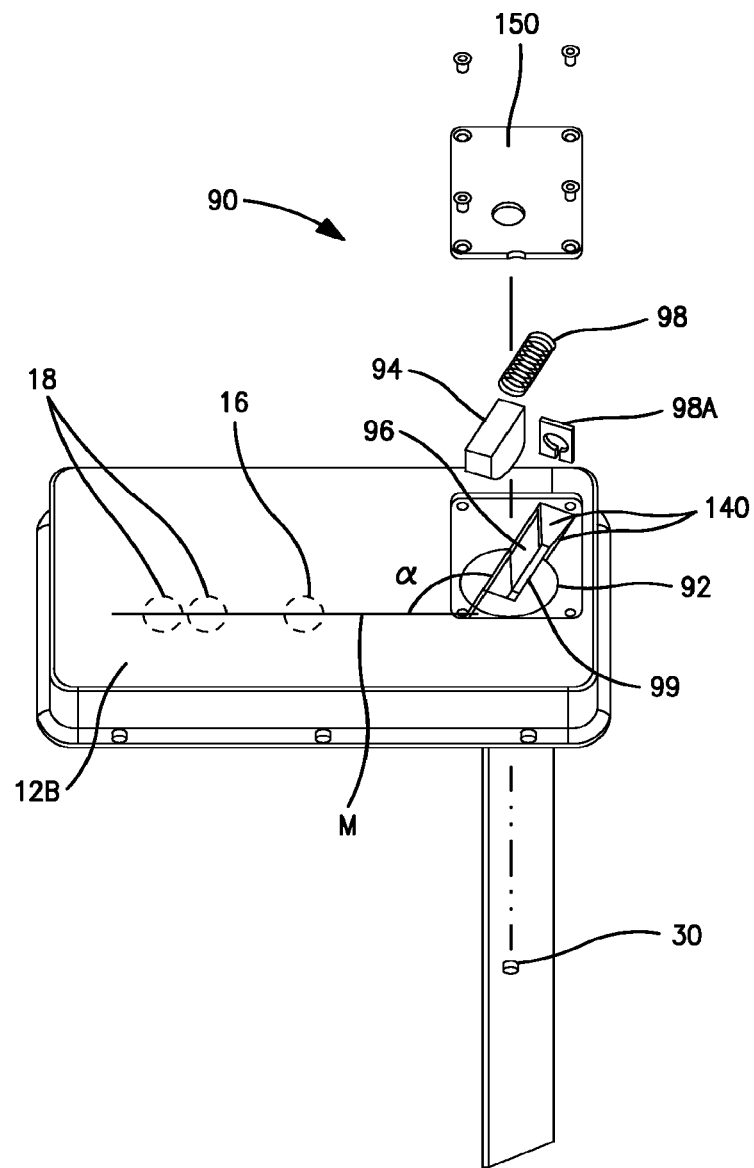
FIG. 17 illustrates a partially exploded bottom view of an embodiment of a nuclear gauge according to the present subject matter.

The track 96 is configured to extend in a direction within the nuclear gauge 10 so that, as the sliding block 94 moves from the first position to the second position, the sliding block 94 moves away from the radiation detector(s) 18A, 18B as shown in FIG. 16 with the sliding block housing 12D'. The track 96 can extend at an angle α of between about 90° and about 180° as measured from a plane M extending between the radiation detector(s) 18A, 18B and the point of the track 96 closest to the radiation detector 18A as shown in FIG. 17. In some embodiments, the track 96 can extend at an angle α of between about 100° and about 135°. The angle α of the track can bias the sliding block 94 toward a closed position due to gravity when the gauge is placed in a carrying case and the carrying case is in its upright position. Further, at such an angle, the effect of the sliding block 94 on the reading of the gauge 10 is minimized as any leakage of radiation is directed away from the detectors.

As stated above, the safety shield can be a molded block. The safety shield 92 can be made of lead. Alternatively, the safety shield 92 can be tungsten or a tungsten and lead mix. For example, the safety shield 92 can comprise concentric cylinders of lead and tungsten. The shield track segment 92B can include two opposing side walls 92D extending into the safety shield 92 and an end wall 92C disposed between the side walls 92D (see FIG. 21) within the safety shield 92 with at least a portion of the end wall 92C within the safety shield 92 comprising a hard surface material. The safety shield 92 can include wear plates, or inserts, of a hard surface material that forms the end wall 92C. The hard surface material can comprise at least one of steel, hardened steel, high carbon steel, stainless steel, tungsten or the like.

Figure 18A:
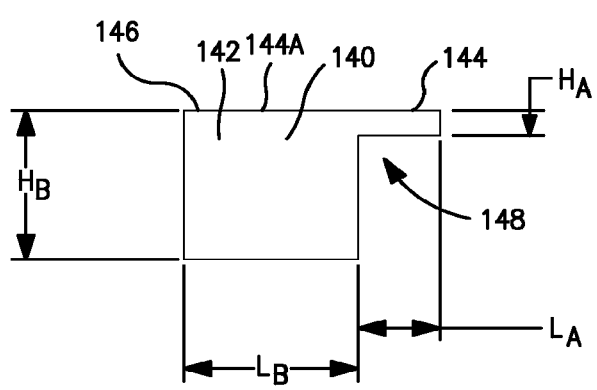
Figure 18A:
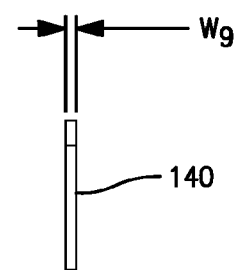
Figure 18A:
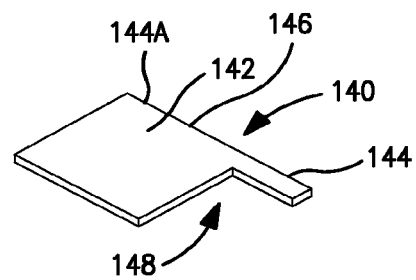
Figure 19:
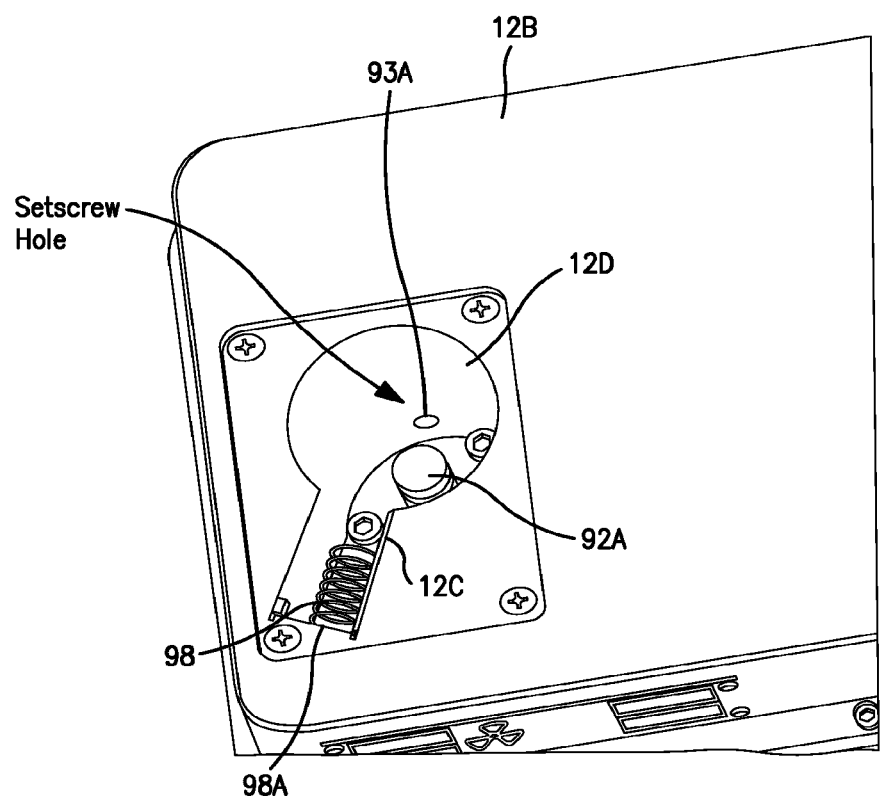
FIGS. 19-24 illustrate partially perspective bottom views of an embodiment of a nuclear gauge and components of a radiation shield assembly according to the present subject matter.
Figure 20:
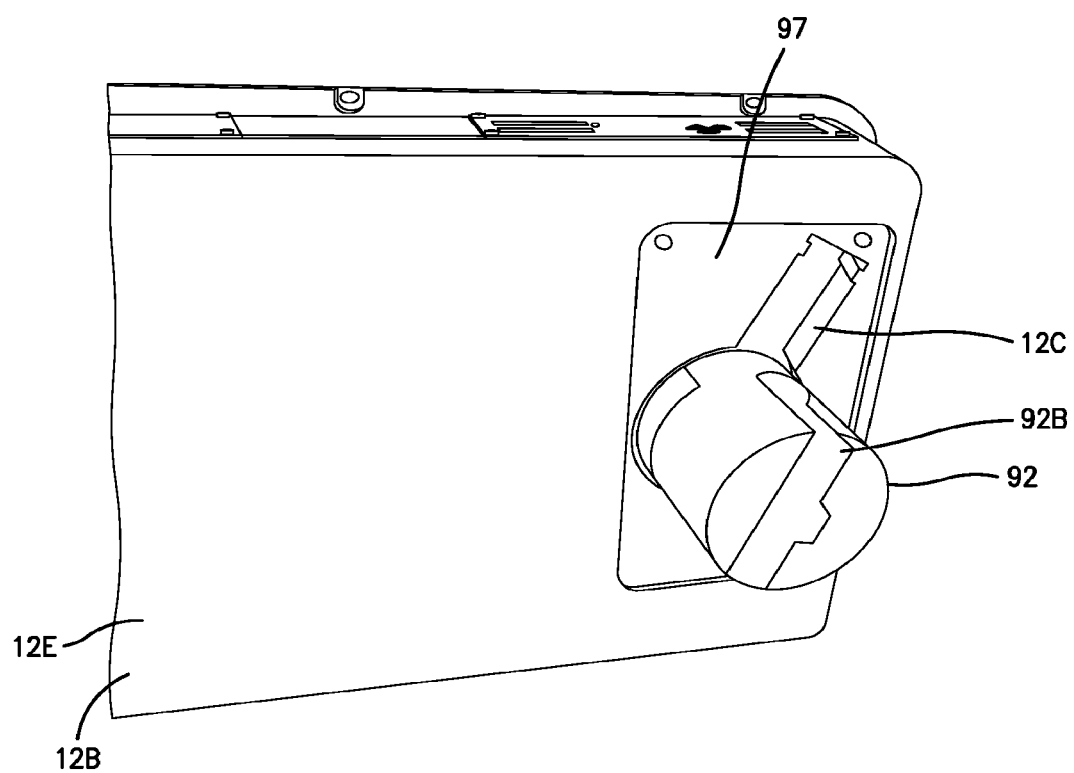

The at least one replaceable sliding guide 140 shown in FIGS. 18A-18C can be or can include a polymer having a low coefficient of friction. The polymer can be at least one of polytetrafluoroethylene, perfluoroalkoxy, and fluorinated ethylene propylene. The at least one replaceable sliding guide 140 can include a body 142 and an arm 144 extending outward from the body 142. The body 142 can include a rectangular shape with a base side 146 and the arm 144 can comprise a different rectangular shape extending from the base side 146, wherein the body 142 has a height that is larger than a height of the arm 144 thereby forming a notch 148 in the at least one replaceable sliding guide 140.

In such embodiments, the safety shield 92 can define an indentation 99, as shown in FIG. 17, configured to receive the arm 144 of the at least one replaceable sliding guide 140 so that an outer surface 140A of the at least one replaceable sliding guide 140 is about flush with an outer surface of shield track segment 92B of the safety shield 92. The arm 144 by engaging the indentation 99 can minimize rotation of the sliding guide 140 in the safety shield 92 caused by movement of the sliding block 94. In embodiments where the base 12B of the gauge housing 12 includes a base track segment 12C and the base track segment 12C and the shield track segment 92B are alignable to form the track 96, the base track segment 12C can have a width that is larger than the width of the shield track segment 92B for receiving the body 142 of the at least one replaceable sliding guide 140.

Figure 24:
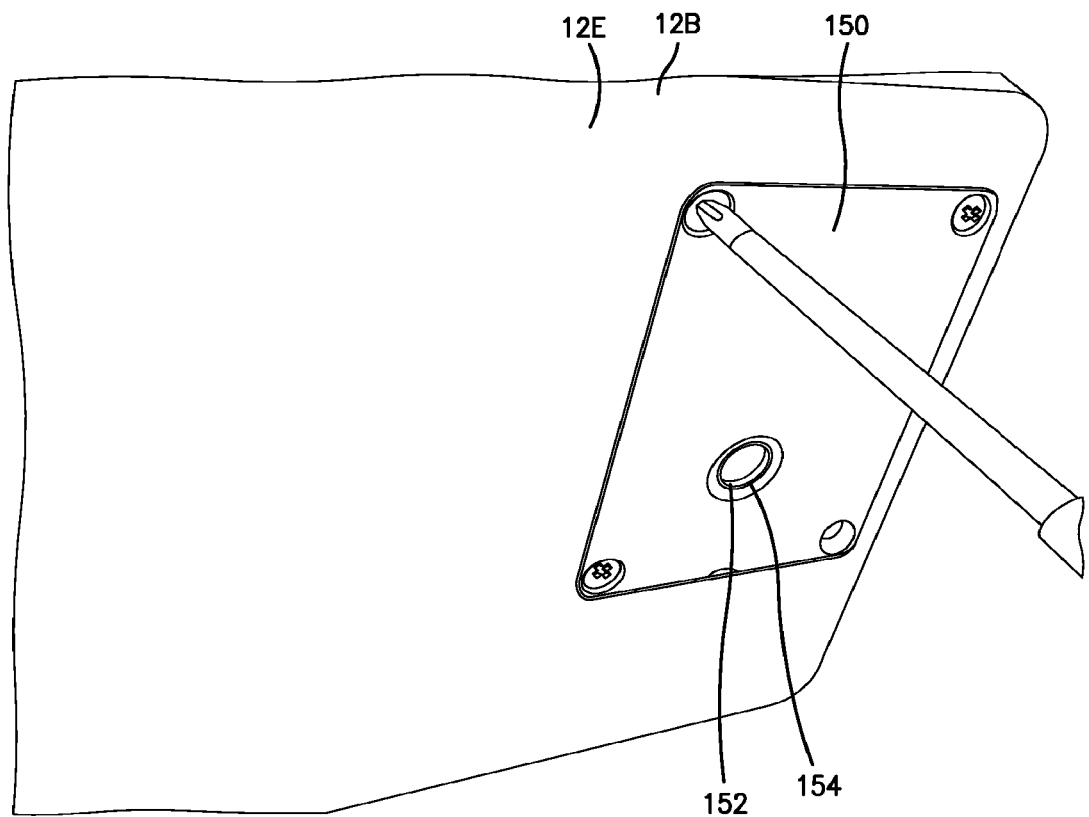
Figure 25A:
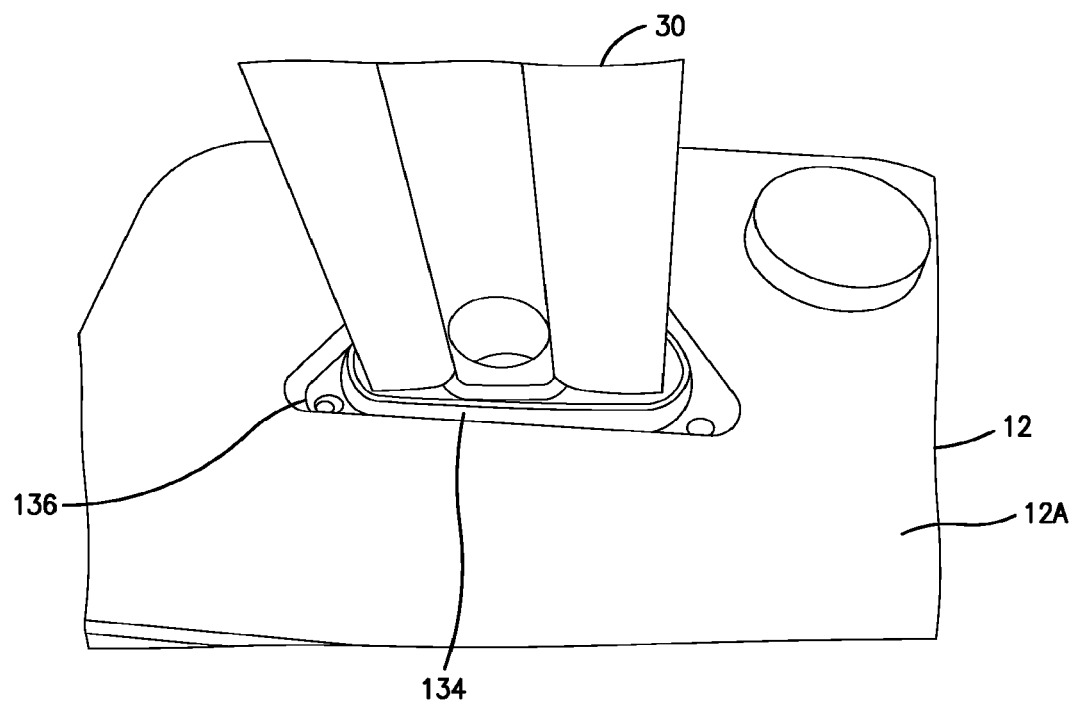
FIGS. 25A-25C illustrate partially perspective views of an embodiment of a nuclear gauge according to the present subject matter.
Figure 25B:
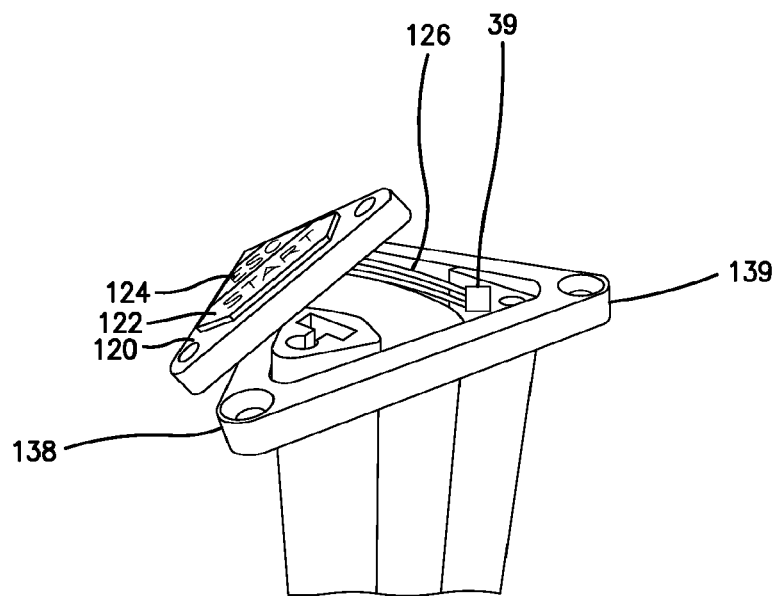
Figure 25C:
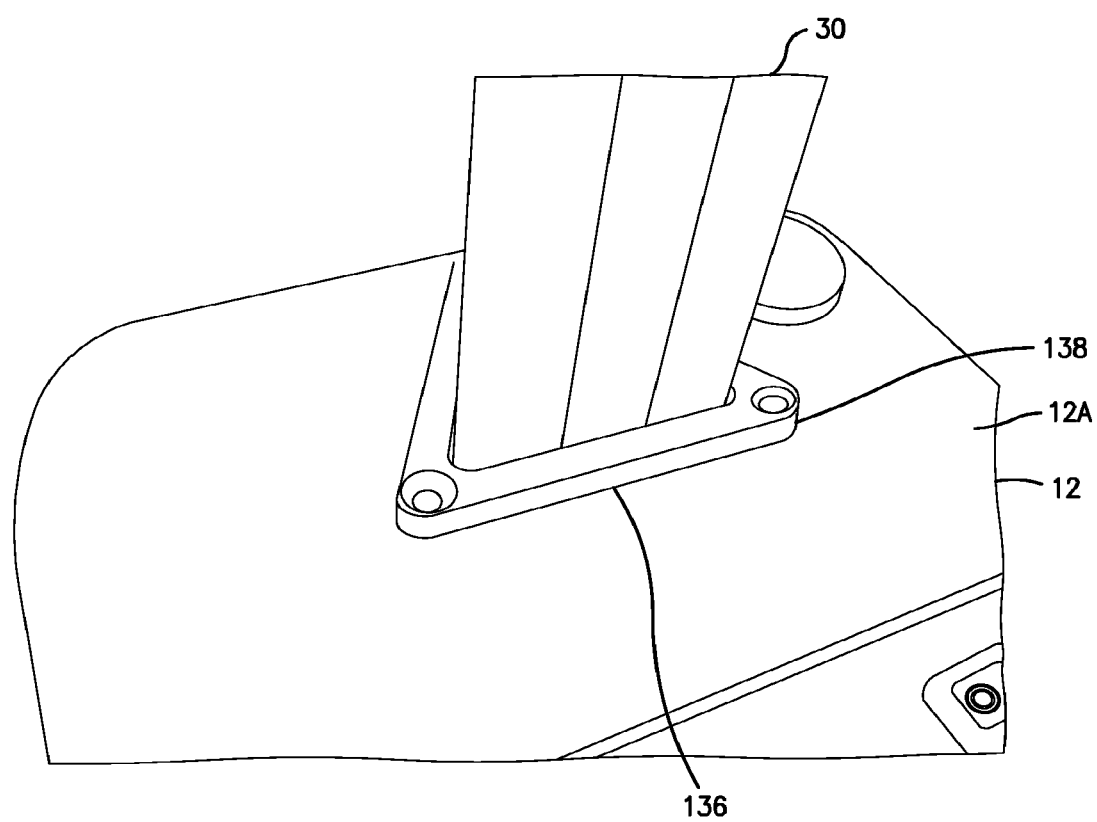

A cover plate 150 for securing the radiation shield assembly 90 within the gauge housing 12 can be included with the radiation shield assembly 90. The cover 150 can be a scraper plate that includes a scraper 152. The scraper ring 152 can be held in place in the cover plate 150 by a ring retainer 154 as shown in FIG. 24. The cover plate 150 can be placed in a recess 97 in the lower surface 12E of the base 12B of the gauge housing 12. Once installed, the cover plate 150 can abut the base side 144A of the at least one replaceable sliding guide 140. The outer surface of the cover plate 150 can be flush with the lower surface 12E of the base 12B. The cover plate 150 is positioned on the base 12B at an angle that covers the rest of the radiation shield assembly 90 and such that the entire radiation shield assembly 90 is contained inside the base 12B underneath the cover plate 150.

Referring back to the remote keypad 120 as shown in FIGS. 1-3 and 25B, such a keypad 120 located at the end of the tower 30 distal from the gauge housing 12 is intended to reduce the amount of bending and/or stooping required by the operator of the gauge 10. The operator's greatest benefit is gained while using the gauge 10 on an asphalt mat in the backscatter position. The operator will identify a measurement location on the asphalt mat. The operator will then move the source rod 20 to the backscatter position of approximately contacting the surface (the transmission mode assumes a BS position of zero, true that it is about 2 inches from safe position, but safe is not zero). The operator can then, with very little movement, press the start switch 122 to initiate the gauge counting. The location of the remote keypad 120 when located on the end of the tower 30 distal from the gauge housing 12 can be approximately two feet off of the asphalt mat and remains at that distance regardless of the source rod position.

Alternatively, the operator can identify the measurement location, place the source rod 20 in the backscatter position and then press a start switch on the user interface 13 of the gauge 12 located on the gauge housing 12. The location of the user interface 13 on the gauge housing 12 is approximately 5 to 6 inches off of the asphalt mat. Typically, to press the start switch on the user interface 13 located on the gauge housing 12 to initiate a gauge count, the operator will have to bend their back all of the way forward or stoop down closer to the asphalt mat to begin a gauge count. While the use of the remote keypad 120 provides a more ergonomically safe method to operate the gauge 10, either the remote keypad 120 or the user interface 13 on the gauge housing 12 can be used.

Thus, the first and second user interfaces 13 and 120 share some functionality with the first and second user interfaces with each including at least one keypad switch having functionality for communicating the same user input to the nuclear gauge computing system. For example, both the remote keypad 120 and the user interface 13 on the gauge housing can share the "start" and "escape" functions in the embodiment shown, since the remote keypad 120 includes both a start switch 122 and an escape switch 124. Electrically, the start switch 122 and escape switch 124 can be wired in parallel to the same two keys on the user interface 13 located on the gauge housing 12. The firmware operating the gauge 10 can be written in a manner that will allow a single key press of the start switch 122 to begin a gauge count and allow the operator to store that gauge count information in a gauge memory in the CPU 17 with an additional single key press of the start switch 122. Alternatively, an I/O interrupt could be initialed by start switch 122 letting the gauge software enter the requested state, such as starting a count or measurement.

The remote keypad 120 can be located on the stationary support tower 30. This tower 30 provides an excellent location for a stationary keypad and a routing compartment 39 to route electrical wiring 126 from the remote keypad 120 into the gauge housing 12 for connection with the CPU 17. Alternatively, the remote keypad 120 can be located on the handle 50. Because the handle 50 moves with the source rod 20, the power source to operate the remote keypad 120 could be contained within the handle 50. For example, a battery can be provided or power can be established with sliding contacts between the gauge 10 and handle 50.

Further, the keypad 120, as stated above, can be an entity totally separate from the physical body of the gauge 10. For example, the remote keypad 120 can be a fob that may be placed on a lanyard that can be hung around the operator's neck. Methods of communication between the CPU 17 in the gauge housing 12 and the remote keypad 120 for such embodiments where the remote keypad is secured to the handle or the remote keypad as a separate entity can be wireless in nature. For example, a transmitter can be located in the handle and a receiver can be located in the gauge housing for embodiments where the remote keypad is located on the handle. For embodiments where the remote keypad is a separate entity such as a fob, a transmitter can be located in the remote keypad and a receiver can be located in the gauge housing. Methods of wireless communications can be established via infrared or RF, BLUETOOTH®, or the like.

Methods of Configuration and Calibration

Described below are methods of calibration and configuration. The methods of configuration and the methods of calibration set forth below are provided by way of example to illustrate embodiments thereof and are not meant to limit the present subject matter. Other methods of configuration and the methods of calibration can be used without deviating from the scope and spirit of the present subject matter. Further, these methods of configuration and methods of calibration can be used on other embodiments of nuclear gauge other than those described above. For example, nuclear gauges similar in construction to those disclosed in U.S. Pat. Nos. 4,525,854, 4,701,868, 4,641,030, 6,310,936 and 6,442,232 can use such methods of configuration and methods of calibration.

Configuration Methods

The same software and CPU can be used with different nuclear gauges. However, there are certain features on some nuclear gauges that are not on other nuclear gauges. In order to restrict access to customers who purchase a nuclear gauge containing fewer features, the gauges must be configured at the factory. This configuration can be done by setting flags in permanent memory that are read by the gauge CPU.

Each of these flags can represent a gauge feature that is variable at manufacturing time. These flags can set different settings for the gauge in which the software is employed. For example, the settings can relate to the source rod length, for example, whether the source rod is an 8-inch unit, a 12-inch unit, or a unit for use on a backscatter only gauge. The settings can relate to the indexing positions, for example, whether the indexing positions are at 1 inch or 2 inch increments. Such settings can also relate to the type and/or model of nuclear gauge, and whether the gauge contains GPS capabilities or not. The owner's identification and contact information, serial number of the gauge and sources can also be stored for retrieval at any time by an authority.

To accomplish this configuration, a program can be written for a computer, such as a personal computer, that allows an assembler to select how the flags are set. This program can also communicate this information to the gauge. These communications can be over the serial port. The assembler setting up the gauge flags can place the gauge in a mode where the gauge is looking for specific commands from the serial port. Then, when the information entered into the program at the computer is correct, a computer command can be started that can take this data and transfer it to the gauge over the serial port using specific commands. The gauge can set the appropriate flags in permanent memory. When the software is executed, these flags can be checked to determine gauge type, source rod and indexing information, and if GPS capabilities are available.

The nuclear gauge 190 that is configurable to operate in a plurality of settings can include a computing system 192. The computing system 192 can be adapted to be configured to enable and to disable the settings of the nuclear gauge 190. A nuclear gauge configuration system 194 can be in communication via a communication connection 196 with the computing system 192 of the nuclear gauge 190. The communication connection 196 can be a wired connection such as a cable connection between serial ports or a wireless connection. At the nuclear gauge configuration system 194, commands can be communicated to the computing system 192 of the nuclear gauge 190 for one of enabling and disabling the settings of the nuclear gauge 190. The commands can be received by the nuclear gauge 190 from the nuclear gauge configuration system 192. Once the commands are received, the setting can be enabled or disabled based on the received commands. The commands can be created by user input at the nuclear gauge configuration system 194 that at least one of the settings of the nuclear gauge 190 is to be enabled and disabled. As stated above, these settings of the nuclear gauge 190 can include a source rod length, indexing positions, gauge type, global positioning system (GPS) operability, calibration curve selection, calibration type, and owner and serial number information.

In addition to the settings determined by the flags set forth above, the settings that can be set using the configuration method can include enabling or disabling diagnostic routines, service information and scheduling, USB port, automatic depth versus manual position detection, and a remote keypad.

Further, the settings that can be set using the configuration method can include the type of calibration that is used in a gauge. For example, the type of calibrations can be a method one calibration (one block), a 5 block calibration, or a 3 block calibration. The calibration of such gauges will be discussed in more detail below. Further, the gauge can be configured to operate with a nuclear gauge calibration device, such as a Troxler Tracker™ device provided by Troxler Electronic Laboratories, Inc., based in Research Triangle Park, N.C., for calibrating a gauge or tracking gauge health. Such a nuclear gauge calibrating device is described in more detail in U.S. Pat. No. 6,369,381 and "The Manual of Operation and Instruction for the Model 6180 Troxler Tracker™ Calibration Tracking System," both of which are incorporated herein by reference in their entirety. The Manual of Operation and Instruction for the Model 6180 Troxler Tracker™ Calibration Tracking System is provided by Troxler Electronic Laboratories, Inc., based in Research Triangle Park, N.C.

An exemplary use of the nuclear gauge calibrating device can be to use it to map a new or newly calibrated gauge response. The obtained data may be stored in the gauge, so that enacting a menu would allow a user to make measurement at a later time on the device and compare results with previously stored data.

Also, an operator of a gauge can also select special calibration curves or corrections for surface roughness or texture, chemical composition of a mix or soils, soil composition, lithography of aggregate material, or corrections for a mix design (e.g., aggregate size and distribution, asphalt content, and the like).

The options, or settings, are enabled and disabled via the software configuration. The options, once selected are reflected in a bit field manipulated by the use of bit masks. Once the bit field is set, it is stored to non-volatile flash memory within the gauge.

Figure 28:
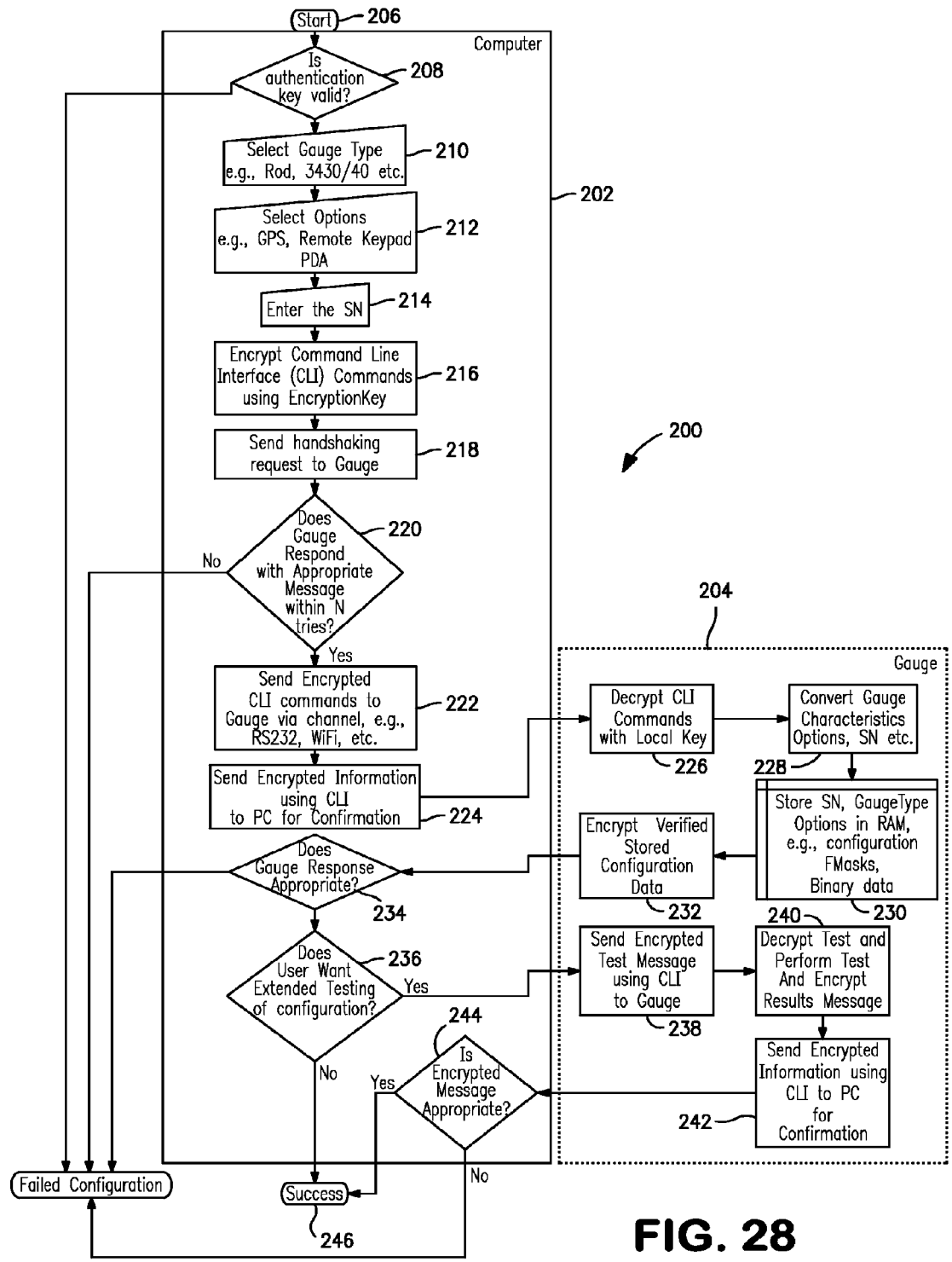
FIG. 28 illustrates a flowchart of an embodiment of a method of configuration of a nuclear gauge according to the present subject matter.

A further example of a configuration method, generally designated 200, is illustrated in FIG. 28. A computer 202 is provided and is in communication with a gauge 204. The configuration is started in step 206 and the authentication key that permits access to the configuration program is validated in step 208. If the authentication key is invalid, then the configuration fails. If the authentication key is valid, the gauge type can be selected in step 210. For example, the gauge can be a density gauge, a bulk density gauge, a thin overlay gauge, a thin layer gauge or a combination thereof. In step 212, other options or features can be selected such as source rod length, indexing positions, and global positioning system (GPS) operability. Also, the options can include enabling diagnostic routines, service information and scheduling, USB port, automatic depth versus manual position detection, calibration curve selection, calibration type, and/or a remote keypad. In step 214, a serial number for the gauge can be entered. The command line interface commands to be sent to the gauge can be encrypted using an encryption key in step 216.

The computer 202 can then make contact with the gauge 204 to start an interface in step 218. For example the computer 202 can send a handshaking request to the nuclear gauge 204. As used herein, handshaking means an automated process of negotiation that dynamically sets parameters of a communications channel established between two entities before normal communication over the channel begins. It follows the physical establishment of the channel and precedes normal information transfer. It is then determined in step 220 whether the gauge 204 has responded with an appropriate message within a set number of tries which can be determined by the manufacturer or user. If not, then the configuration fails. If the gauge 204 does respond, then the encrypted command line interface (CLI) commands are sent to the gauge 204 through a communication connection, such as an RS232, WIFI, or the like. In step 224, encrypted information can be sent to the computer for confirmation. A CLI program can be used for such function.

The commands from the computer 202 can now be received by the gauge 204. The CLI commands are decrypted with a local key in the gauge in step 226. This key can be common to all gauges of a particular series or serial numbers or rely on a hardware key in the USB port such as a dongle. The encryption scheme can be based either on symmetric key technique, an asymmetric technique such as public-private key technique, or a combination thereof. Moreover, the key can be associated with the authentication scheme. Examples of encryption scheme include and are not limited to Pretty Good Privacy (PGP®), gnu privacy guard, ElGamal, DSA, RSA, AES, 3DES, Blowfish, Twofish. The authentication scheme or key enables the possibility to grant the ability to edit, read, and/or set all or a selection of option flags and related information. Depending on the authentication information or key, the flags and data stored in the gauge may be edited or not, read or not. For example only certified centers/users may be able to change the calibration constants and dates.

The commands are then converted in step 228. The section made on the computer are then stored on the gauge in the random access memory (RAM), or non volatile memory such as flash or E-PROM memory of the gauge in step 230. This verified stored configuration data is encrypted in step 232 and sent back to the computer 202 from the gauge 204. In step 234, the computer 202 checks to see if the gauge's response is appropriate. If the response is not appropriate, then the configuration fails. If the response is appropriate, then the computer 202 can determine whether or not the gauge 204 requests extended testing of the configuration in step 236. If not, then the configuration ends successfully at 246. If extended testing is requested, then the computer 202 in step 238 sends an encrypted test message using CLI to the gauge 204. The test message is decrypted and the test is performed and results encrypted in step 240. The encrypted information using the CLI in step 242 is sent back to the computer 202 for confirmation. The encrypted message is checked by the computer 202 to determine whether it is an appropriate response in 244. If it is, then the configuration is successfully complete in 246. If the message is not appropriate, then the configuration fails.

Other similar configuration methods can also be performed between a configuration device such as a computer and the computing system of the nuclear gauge.

Calibration Methods

Normally, in nuclear gauges used to determine moisture and/or density of the materials, calibration has been completed by information gathered and entered by the person attempting the calibration. Calibration constants needed for the operation of the gauge are calculated and manually entered. Thus, there exists the great possibility that erroneous contacts are entered, thereby leading to a greater opportunity of poor quality calibration that in turn can lead to false readings by the nuclear gauges.

To increase the quality of calibration, the option to manually enter calibration constants manually can be eliminated. Calibration can be achieved through the use of a computer, such as a personal computer, containing software applications and a Command Line Interpreter (CLI) function located in the gauge. For example, the CLI can be a software application that is stored along with other software applications on the computing system of the gauge. Once the computer and gauge are in communication with one another, through wireless or wired communications, the computer can interrogate the computing system, including the memory, of a nuclear gauge for information needed to calibrate the nuclear gauge. This information can include, for example, current index, counts, or the like. The computer can collect all of the relevant information and calculate calibration constants. Calibration constants can then be downloaded to the gauge via the CLI. All communications between the gauge and the computer can be encrypted.

Figure 29:
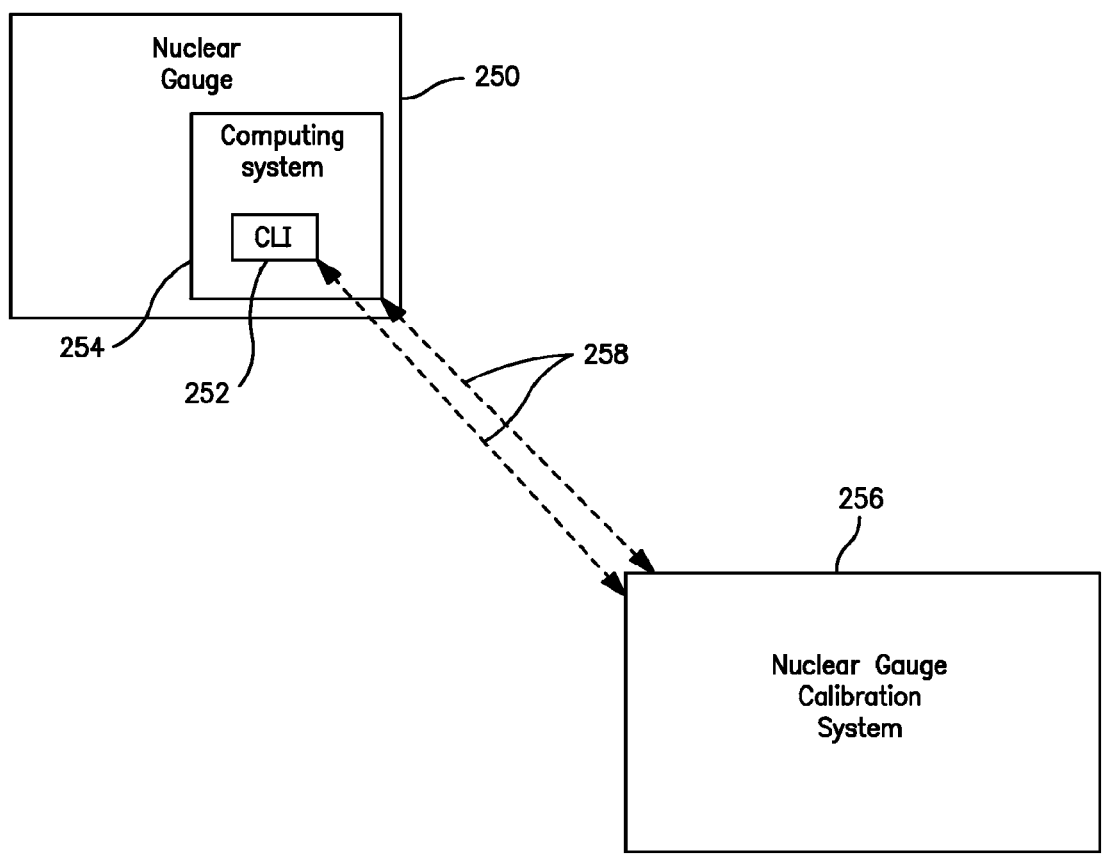
FIG. 29 illustrates a schematic view of an embodiment of a nuclear gauge in communication with a nuclear gauge calibration system according to the present subject matter.

A method for calibrating a nuclear gauge 250 as shown in FIG. 29 can include providing a nuclear gauge 250 adapted to be remotely calibrated via encrypted calibration communications. The nuclear gauge 250 can include a command line interpreter 252 adapted for receiving calibration commands. The command line interpreter 252 can be hardware or a software program that provides a command line interpreter function. A nuclear gauge calibration system 256 in communication with the computing system 254 of the nuclear gauge 250 can also be provided. The nuclear gauge calibration system 256 can be connected to the computing system 254 of the gauge 250 by a communication connection 258. The communication connection 258 can be a wired connection or a wireless connection as described above. The nuclear gauge calibration system 256 can be adapted to interrogate the nuclear gauge 250 for calibration information. The nuclear gauge calibration system 256 can communicate encrypted commands to the nuclear gauge 250 for calibrating the nuclear gauge 250. The calibration information can include current index, counts, or like. The calibration information can also include gauge type, serial number of gauge, serial number of sources, date, time, calibration constants, technician, calibration location, calibration type, type of material being calibrated.

The calibration information from the nuclear gauge is communicated in an encrypted format to the nuclear gauge calibration system. The nuclear gauge calibration system can then calculate calibration constants based on the calibration information, and communicate the calibration constants to the nuclear gauge in an encrypted format. All communications between the nuclear gauge and the nuclear gauge calibration system can be encrypted.

Figure 30:
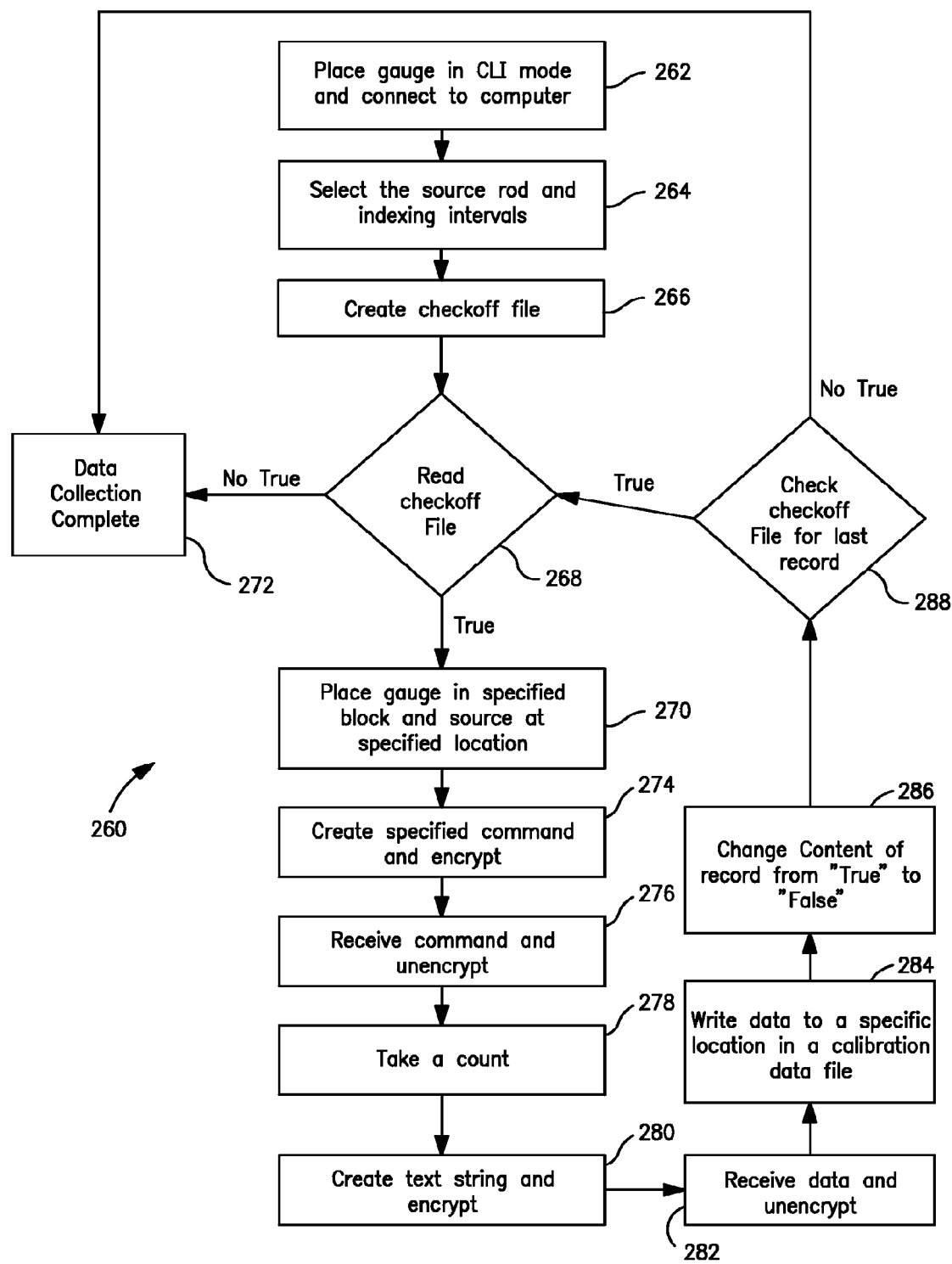
FIG. 30 illustrates a flowchart of an embodiment of a method of calibration of a nuclear gauge according to the present subject matter.

For example, as shown in FIG. 30, a calibration method generally designated 260 can be provided. In step 262, the gauge can be placed in CLI mode and connected to the computer via a communication cable, such as an RS232 cable. From a computer program on the computer, a calibration technician can select the source rod size and indexing intervals for the gauge to be calibrated in step 264. Further, calibration technician can select the type of calibration (3 block or using a nuclear gauge calibration device, soil or asphalt), date, time, location, the duration of the count time, or the like. A "checkoff" file (structured random file format) can be created in step 266 based on the data information selected by the technician. If a particular count or series of counts is required, then the record in the file corresponding to that count or series of counts can be set to True; otherwise, it can be set to False. In step 268, the calibration program in the computer can begin reading the checkoff file from a first record, and can read down until a "True" record is encountered. Based on the location of this "True" record, the user in step 270 is prompted to place the gauge on a specific block (or a poly standard block for the stat or drift test), place the source rod in a specific location and click a switch on the computer. In the event that no "True" record is found, then the data collection process for the calibration is complete in step 272.

Based on the location of the current record in the checkoff file, the computer can create the specific command that the gauge needs to initiate a count of a specific time duration in step 274. This command can be encrypted and then sent to the gauge through a communication port such as an RS232 port. The gauge can receive this encrypted command and can un-encrypt it in step 276. The gauge then can take a count that has the count duration indicated in this un-encrypted command in step 278. When the gauge concludes the count that was initiated, the gauge can take the results of the counts, create a text string, and encrypt the text string in step 280. This text string can be sent by the gauge to the computer via the communication port. The computer, which can begin waiting for a reply from the gauge a few seconds before the count is scheduled to finish, can receive the encrypted data from the gauge and un-encrypts the data in step 282. The computer can write the unencrypted data to a specific record location in a calibration data file in step 284. The computer can change the content of the current record in the checkoff file from "True" to "False" in step 286. In step 288, it can be determined if the current record was the last record in the checkoff file. If the current record in the checkoff file is the last record, then the data collection process for the calibration is complete. If the current record in the checkoff file is not the last record, then the program goes back to step 268 and begins reading the checkoff file again to initiate the collection of more data.

As stated above, diagnostics of the health of the gauge that look at parameters such as the typical calibration constants, count rate, precision and slope as a function of density of each gauge, along with their standard deviations have in the past been performed only at the factory. In the factory, external computer networks are wired to each calibration bay, the data is transferred by wire from the instrument to the external computer, where computer programs known in the art are used to curve fit, transfer the coefficients, store the coefficients to the gauge, and quality control check each measurement for deviations out of the standard expected values. The computing system of the gauge can have the ability to perform all these external factory functions, yet not need an external network to do so. The computing system of the gauge can accomplish this by having increased functionality and the associated computing power and memory needed to do it.

Generally, different methods of calibrating the density measurement system can be used including the method one calibration, the three-block calibration, or the five-block calibration. The three-block calibration and the one block calibration are described in more detail below. Further, a method of calibrating the moisture measurement system can also be used.

The calibration of a gauge is a combination of several independent sets of measurements and calculations. A separate calibration should be performed at each source rod position (depth). Consequently, a complete gauge density calibration can consist of up to twelve separate and independent calibrations. Each source rod position of each gauge has its own unique set of three density calibration constants. One of the main goals of the calibration process is to determine the calibration constants for each source rod position for a given gauge. Ideally, a gauge can be calibrated for the specific soil in which it is to be used. However, for typical construction soils, and for gamma rays, the differences in composition from one soil to the next are usually, but not always, small. Therefore, gauges are calibrated using a representation of an "average" soil.

To avoid problems with soil standards, a combination of metallic blocks can be used as calibration standards. These blocks are homogenous throughout, do not absorb significant amounts of moisture, retain their physical dimensions and surface integrity after repeated contact with gauges, and maintain their densities well. The materials that make up these blocks are quite different from average soil. However, when calibrating a gauge, mathematical adjustments are performed to compensate for the differences in elemental composition between the blocks and average soil. These adjustments enable the blocks to "look like" average soil.

Three-Block Calibration:

The Three-Block Calibration method has been accepted and implemented by the American Society for Testing and Materials (ASTM) as ASTM standard: ASTM D7013-04, which is incorporated herein in its entirety. In the Three-Block Calibration, the gauge is placed on three standard blocks of known density: a magnesium block, an aluminum block, and a block made up of alternating sheets of magnesium and aluminum. For each standard block, the density count is taken at each source rod depth. The counts from each block at each depth are then used to calculate the calibration constants for the gauge. The attenuation of gamma rays through a material is related to the count ratio, which is the ration between a standard count $C_{std}$ and the measurement count $C_m$. Here, for each position, the measurement count is attenuated through the material as a function of its density as:

$$C_{std}/C_{std} = A\ e^{-Bx} + C$$

Where:
X is the distance between the source and detectors;
B accounts for the material properties such as density and chemical composition including where some photons are absorbed; and
A and C relate to the geometry of the instrument.

In calibration, a measurement at a particular position such as 6 inches is performed at three densities, and thus 3 equations and 3 unknowns are used to solve for A, B, and C at each position. These solutions are found by the usual methods such as the method of least squares, or a direct curve fit using matrices and determinants.

Method One Calibration:

A method one calibration is only used for established gauge models after sufficient data has been collected for that gauge model and a group of coefficients can be determined that define a linear relationship between any two of the density counts obtained in a Three-Block Calibration for that gauge model. A Method One Calibration uses only the magnesium/aluminum block to calculate the calibration constants. A density count is obtained at each source rod position. The density count and the coefficients for the gauge model are used to calculate the density counts for the magnesium and aluminum blocks. The results are then used to determine the calibration constants for that source rod depth. In this method, only a single density measurement is obtained, and for each geometry a curve is defined assuming higher and lower density count responses. Hence, at each position, a quality control step must be implemented where actual measurements on magnesium and aluminum (higher and lower densities) are physically checked. This method is simply a production time saver for calibration.

Moisture Calibration:

The calibration of the moisture measurement system includes three measurements: a moisture standard count and two other moisture responses. These measurements are taken using the magnesium block (0% moisture) and a block made up of alternating sheets of magnesium and polyethylene representing (moisture). Typically, the moisture value of the magnesium/polyethylene blocks used in such calibrations is between 561 kg/m3 (35 pcf) and 625 kg/m3 (39 pcf).

After moisture counts have been taken on the magnesium and magnesium/polyethylene blocks, the results are used to determine two moisture calibration constants, as typically this is a linear equation.

Applying Calibration Constants:

After a gauge has been calibrated and its calibration constants have been determined, the constants are loaded into the gauge memory. The gauge is then used to perform a series of quality assurance measurements to verify the operation of the gauge. The gauge is used to measure a number of blocks with known density and moisture values. On each block, a density measurement is taken at each source rod position. If the gauge reads the correct density value within 1 lbs./ft.$^3$ (pcf), the calibration for that source rod position is considered accurate. If the measured density is incorrect, the density calibration for that source rod position is repeated.

Similarly, the gauge is used to measure the moisture on a magnesium/polyethylene block. If the gauge reads the correct moisture value within 1 pcf, the moisture calibration is considered accurate. If the moisture measurement is incorrect, the moisture calibration is repeated. When the gauge has passed all density calibration tests and the moisture calibration tests, it is ready to be shipped.

The calibration blocks used to calibrate such gauges can be calibrated using NIST-traceable standards. The gravimetric densities of these blocks are found using the dimensions and mass of each calibration block. These blocks are referred to as the Primary Calibration Standard Blocks. The complete set of primary blocks can be used to perform a high-precision Three-Block Calibration and calibration confirmation on a gauge. This gauge is then referred to as a master gauge and is used to quickly measure a traceable density of other calibration blocks without the tedious dimensional and mass measurements.

Figure 31:
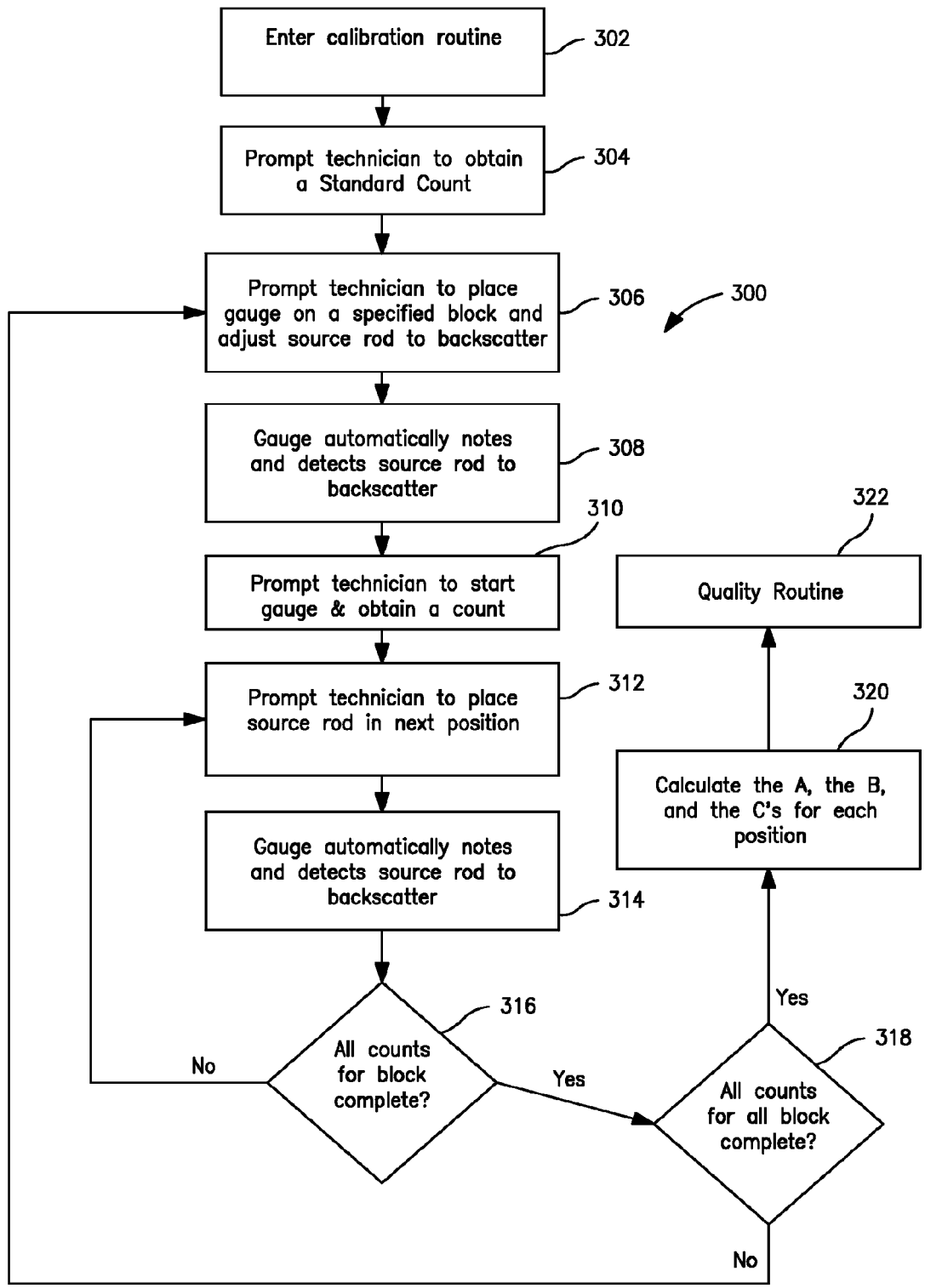
FIG. 31 illustrates a flowchart of an embodiment of a method of calibration of a nuclear gauge according to the present subject matter.

The computing system of the gauge through embedded software can facilitate the performance of a calibration method 300 as shown in FIG. 31. A calibration routine can be entered in step 302. A technician working with the nuclear gauge to carry out the calibration can be prompted to obtain a standard count in step 304. This prompt can take place on the LCD screen on the user interface of the gauge. In step 306, the technician is prompted, for example, through the LCD screen, to place the gauge on the first (magnesium block) and adjust the source rod to a backscatter, or the first position. At step 308, the gauge automatically notes and detects that the source is in backscatter position, and adjusts the counting time accordingly. The program can then prompt the technician in step 310 to hit the "start" switch, whereby the gauge obtains a count, and stores this value in its computing system memory.

At the conclusion of the count in step 312, the program can prompt the technician to place the source in a second position. Upon the activation of the "start" switch for a second count, the gauge can automatically select the time for the measurement at this second position. The gauge obtains a count at this second position, and stores this value in its computing system memory. In step 316, it can be determined whether all the counts for the specified block are complete. If not, the steps 312 through 314 can be repeated until all the counts within this first density block are completed and all counts have been recorded in the gauge. If all the counts for the first density block are collected and stored, it can be determined if all the counts for the other density blocks have been taken in step 318. If not, the technician can then be prompted to move the gauge to the next density block and the steps 306 through 316 can be repeated. At the end of taking all density measurements and desired positions, the gauge can perform its own calibration calculating the A, the B, and the C's for each position thus establishing the calibration curves for each desired position in step 320. The gauge then can perform a quality control routine in step 322.

Figure 32:
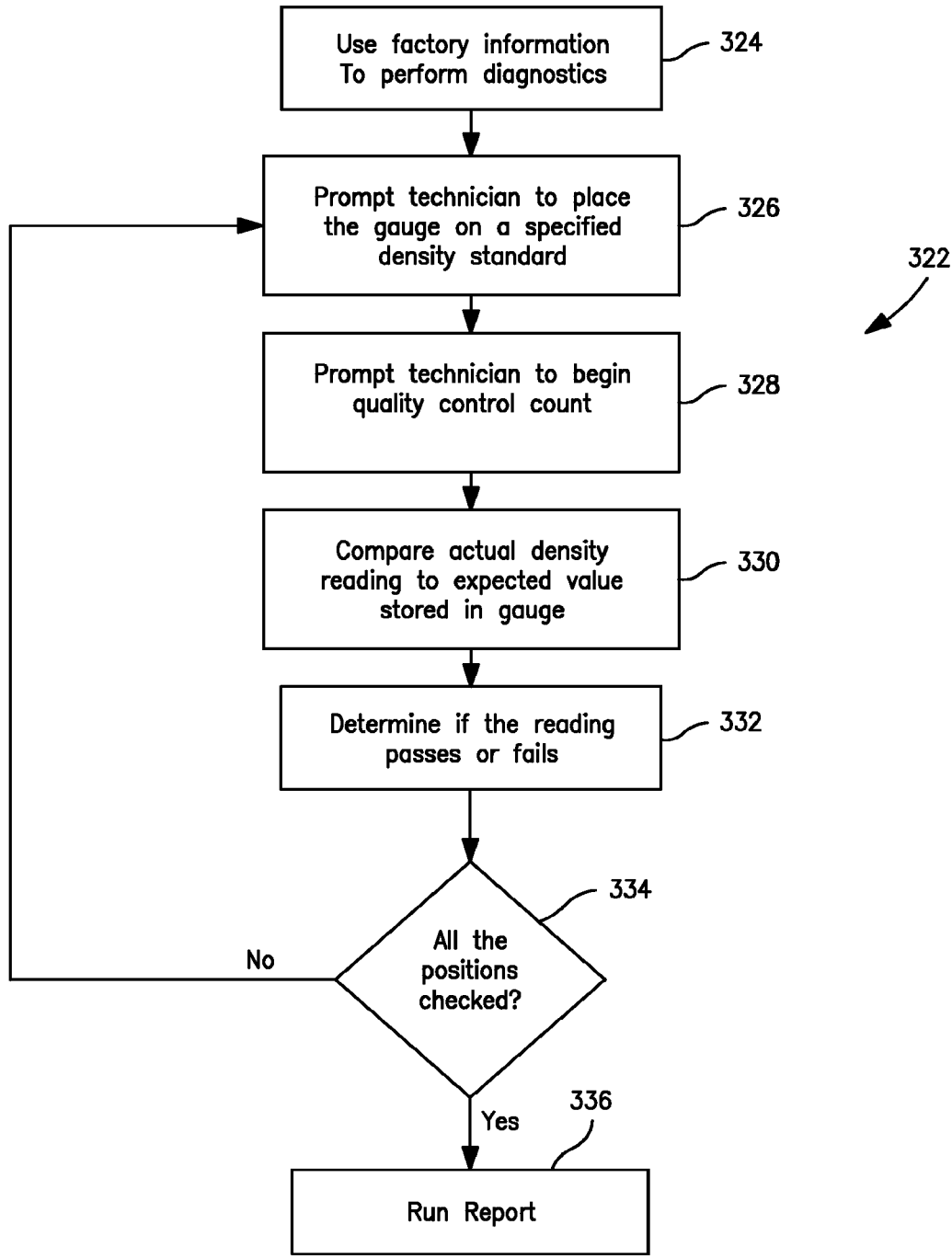
FIG. 32 illustrates a flowchart of a partial embodiment of a method of calibration of a nuclear gauge according to the present subject matter.

As shown in FIG. 32, the computing system can also carry out the quality control routine 322. The quality control routine can use factory information stored inside the gauge to perform diagnostics such as analyzing the coefficients of each curve for slope, count rate, precision and standard deviation in step 324. In particular, this factory information is standard information that can be downloaded before the nuclear gauge is used or before the information is needed. Thus, this previously downloaded standard information can be useful in perform diagnostics on the gauge. Provided that all diagnostics are in good order, the gauge in step 326 can then prompt the technician to place the gauge on a certain density standard. Once the gauge is properly placed, the gauge can prompt the technician to begin a quality control count in step 328. At this point in step 330, the gauge can compare the actual density measured by the gauge at this position to the expected value stored in the gauge. In step 332, the gauge can then decide whether the measurement passes or fails. In the step 334, it can be determined if all the positions are checked. If not, the technician can be asked to move the gauge to the next position. If all the positions are checked, a full report can be displayed by the gauge on the LCD screen, printed to paper, or stored in a portable USB memory for transfer to a host computer in step 336. This full report suggests which positions should be recalibrated, or if a possible problem might exist in the mechanical or electrical components of the gauge.

This internal calibration capability can reduce the cost of much equipment needed for calibration, not to mention the frustrating interconnect problems and data transfer that is associated with current methods. The internal calibration capability can provide economical, frustration-free calibration, quality control and diagnostics not only for factory technicians but for interested users that have the capability and traceable standards necessary for calibration. Users can purchase the rights to access the embedded program, perform their own calibrations, and transfer the results to an external memory or computer device, if desired. Users can also, via the internet, send their results to the factory for further analysis or storage.

Gauge Calibration Performed Internally by Gauge Base on Information Provided by a Nuclear Gauge Calibrating Device:

Although this description incorporates the use of one or more heavy, non-portable calibration blocks, there is an alternative for field analysis and calibration using simulated scaled down calibration standards such as the multipoint nuclear gauge calibrating device or a single point device, both of which are described in U.S. Pat. No. 6,369,381.

Note that the density values from a nuclear gauge calibrating device, such as the device sold under the name TRACKER™ by Troxler Electronic Laboratories, Inc. of Research Triangle Park, N.C., can also be stored in the memory of the computing system of the gauge. Also, the self-calibration described above can be accomplished using a field calibration/verification device instead of the multiple metal blocks described above.

Typically, to confirm the density calibration of the gauge at a given depth the confirmation program that is stored and can be executed in the computing system of the gauge can be entered. The gauge can prompt the user, for example, through the LCD screen to do the following:

1. Place the gauge on the nuclear gauge calibrating device.
2. Set the source rod to the depth suggested by the program on the gauge and displayed on the LCD screen of the gauge.
3. Select the desired index wheel position on the nuclear gauge calibration device from a calibration sheet, such as a TRACKER™ Calibration Sheet provided by Troxler Electronics Laboratories, inc., located in Research Triangle Park, N.C., and move the index wheel to the selected position. The index wheel should click into the detent for the selected position. The index wheel can be a circular disc on the nuclear gauge calibration device that has 5 detented positions where the user looks up the source rod position and finds 3 positions (from the 5 offered) that give low, medium and high density simulations. The index wheel can be physically spun to the required density. Alternatively, an automated index wheel can have a stepping motor on it. Here, the calibration routine automatically gets the three densities for each source rod position, then prompts for the technician to move the rod to the next position.
4. At the gauge, set the recommended count time and obtain a density measurement.
5. Compare the measured density to the density stored in the calibration sheet residing in the memory of the gauge for the selected depth and index wheel position using the internal program of the gauge. If the measured density is within ±2 pcf of the value listed on the calibration sheet, the gauge calibration for that depth and that density can be acknowledged as accepted, accurate or a pass. If the difference between the measured density and the listed value is greater than 2 pcf, the internal software of the gauge can repeat step 4 using a longer count time. If the difference between the measured and listed densities is still greater than 2 pcf, the output of the gauge will suggest and note that this position should be recalibrated.

To confirm the moisture calibration of the gauge, the software can check the moisture measurement on the moisture standard of the nuclear gauge calibrating device. Here, the gauge can select a count time, ask the user to place the gauge on the nuclear gauge calibrating device, and select the "start" switch. At the conclusion of the count, the gauge can compare the measured moisture to the moisture calibration value shown on nuclear gauge calibrating device calibration sheet stored in gauge memory. If the measured moisture is within ±2 pcf of the value listed on the calibration sheet, the gauge moisture calibration is accepted as accurate. If the difference between the measured moisture and the listed value is greater than 2 pcf, another moisture measurement can be taken, preferably using a longer count time. If the difference between the measured and listed values is still greater than 2 pcf, the gauge can suggest that it should be placed in the calibration mode and recalibrated.

Gauge tracking is a powerful method of monitoring changes in the response of a gauge. A packet of density and moisture tracking charts can be supplied with each nuclear gauge calibrating device for manual observations. These charts can be used to record the results of the confirmation measurements performed on a gauge. Any changes in gauge response over time will be reflected on the tracking charts. Conversely, with the processor and memory contained on the gauge, these charts can be stored, manipulated, and monitored by the gauge itself.

With each nuclear gauge calibrating device, comes an assignment of densities found using a master gauge, which can be created as described above. Since the density assignments are made with a second master gauge, and not the particular production gauge that a customer owns, the density values of the nuclear gauge calibrating device can be slightly different than what a perfectly calibrated production gauge would read. This statistical variation is the result of the energy response of each gauge, coupled with any geometrical differences between gauges, and the finite volume of a simulated calibration device like the TRACKER™.

To overcome tracking errors, which can be up to 5 pcf, the software stored on the computing system of the gauge can have the ability to assign its own densities to the nuclear gauge calibrating device. Hence, the nuclear gauge calibrating device and matched gauge will generally read the same, or within a few tenths of a pcf, for example, between about 0.05 pcf to about 0.5 pcf. To enable this feature, the user can enter the "define tracking values" menu of the gauge, and follow the instructions by the gauge as displayed on the LCD screen.

For example, the gauge can prompt the user to input the serial number of the nuclear gauge calibrating device, the user name and gauge serial number. The gauge can prompt the user to place the gauge on the nuclear gauge calibrating device and put the source rod at a specified depth. Further, the gauge can prompt the user to place the index wheel or density of the nuclear gauge calibrating device at the proper position for that gauge model and depth. The gauge can then select a counting time and ask the user to start the measurement. At the end of the measurement, the gauge can store the density of the nuclear gauge calibrating device in its memory, and ask the user to place the source rod and nuclear gauge calibrating device density at the next position. At the conclusion of all desired source rod and density positions, an internal memory map of the values from the particular nuclear gauge calibrating device, and particular gauge can be stored in the gauge. Conversely, instead of exact density values, corrections to the density values supplied by the factory can be stored. Note that this new table of densities is not a general assignment like the factory values, but is particular for this exact gauge serial number for which the tests were run.

This internal map can be used for future diagnostics or "tracking" of this particular gauge. In later tracking use, the technician can enter the serial number of the nuclear gauge calibrating device, and the gauge would check this number with that stored serial number which defined the tracking density map. If these serial numbers agree, the gauge can prompt the technician to place the gauge on the nuclear gauge calibrating device, and begin measurements. These measurements can be stored at future dates, and an actual graph of the calibrating device-gauge matched results measured against time can be produced as an output of the gauge.

For example, if the technician has a daily assignment to measure the soil density and moisture at 6 inches on-site, he can call up the conformation or tracking program internal to the gauge, select the 6-inch position on the keypad, place the unit on the nuclear gauge calibrating device, input the nuclear gauge calibrating device serial number and press a "start" switch. The gauge can select the counting time and commence a measurement. The gauge can then compare this measurement to the value that the gauge gave in its history, and can confirm the quality of the calibration.

Figure 33:
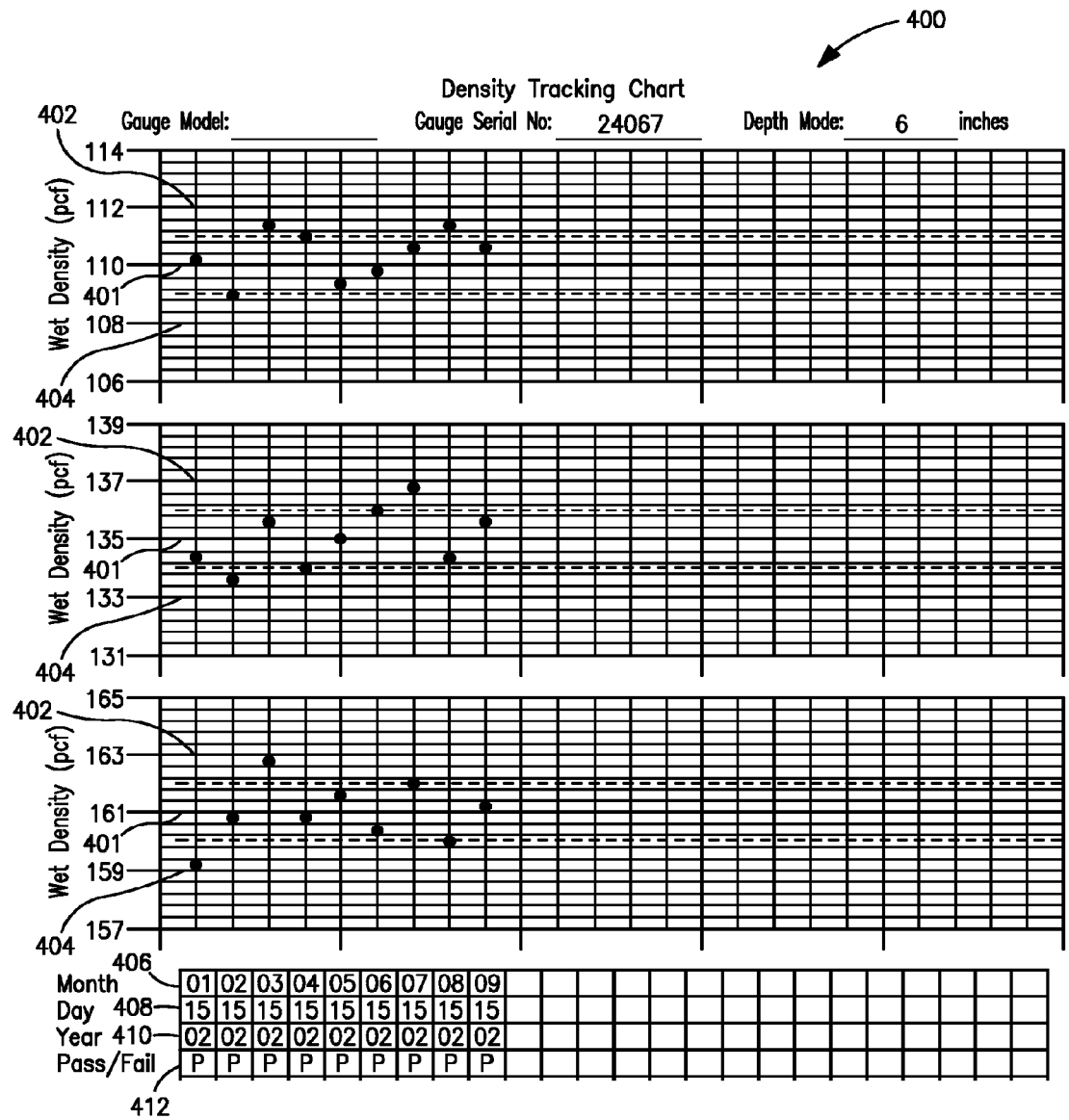
FIG. 33 illustrates an embodiment of a density tracking chart that can be use in an embodiment of a method of calibration of a nuclear gauge according to the present subject matter.

For tracking purposes, a density tracking chart 400 as shown in FIG. 33 can be used. The Y-axis of each grid is incremented in units of 1 pcf above and below the density calibration value represented by the centerlines 401. The solid lines 402, 404 on each grid represent the upper and lower acceptable density values, respectively. In this example, these limit lines 402, 404, are defined as the listed density calibration value ±2 pcf. For example, in the upper grid, the centerline 401 represents 110.4 pcf. The upper limit line 402, therefore, represents a value of approximately 112.4 pcf and the lower limit line 404 represents a value of approximately 108.4 pcf.

The gauge can also record the measurement date including the month in spaces 406, the day in spaces 408, and year in spaces 410 for the density tracking chart 400. The gauge can instruct the user to perform a density calibration confirmation at the different index wheel positions. The gauge can plot each measured value on the appropriate grid. The gauge can also record whether the confirmation passed (P) or failed (F) in the spaces 412 provided at the bottom of the chart. Such a density tracking chart 400 can be displayed by the LCD screen on the gauge, printed or stored on the USB for transfer to another medium.

Figure 34:
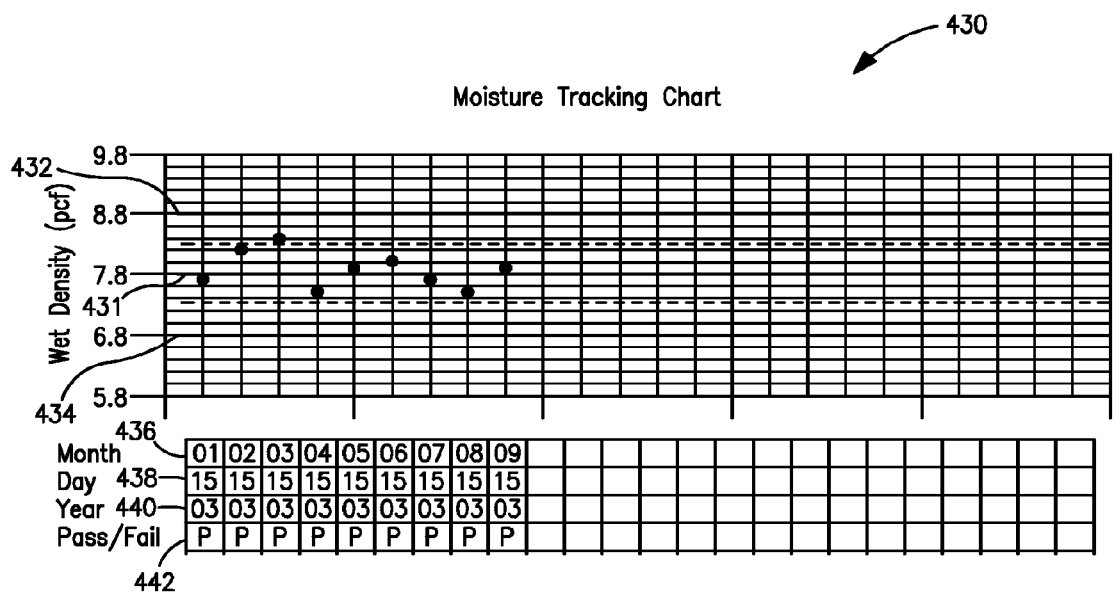
FIG. 34 illustrates an embodiment of a moisture tracking chart that can be use in an embodiment of a method of calibration of a nuclear gauge according to the present subject matter.

FIG. 34 shows a sample moisture tracking chart 430 that can be displayed by the LCD screen of the gauge as well. The chart 430 is used to internally log the moisture calibration measurements, which are not dependent upon the source rod depth. The centerline 431 can represent the moisture calibration value. As with the density tracking chart 400, the Y-axis is incremented in units of 1 pcf above and below the centerline 431 that represents the moisture calibration value. The solid lines 432, 434 on the grid represent the upper and lower acceptable moisture values, respectively upper and lower acceptable moisture values represented by the solid lines 432, 434 are defined as the listed moisture calibration value ±1 pcf. For example, as described above, the centerline 431 represents 7.8 pcf. The upper limit represented by solid line 432, therefore, is 8.8 pcf and the lower limit represented by solid line 434 is 6.8 pcf. As with the density tracking chart 400, the gauge will record the measurement date the measurement date including the month in spaces 436, the day in spaces 438, and year in spaces 440 for the moisture tracking chart 430. Through its software, the gauge can instruct the user, for example on the LCD screen to perform a moisture calibration confirmation. The gauge can plot each measured value on the appropriate grid. The gauge can also record whether the confirmation passed (P) or failed (F) in the spaces 442 provided at the bottom of the moisture tracking chart 430.

As a general rule, when reviewing the density and moisture tracking charts, 95% of the data points on the tracking chart should fall within the upper and lower limit lines. If a data point falls outside the limits, and remains outside the limits during repeated tests, the gauge response has changed and the gauge should be re-calibrated.

Embodiments of the present disclosure shown in the drawings and described above are exemplary of numerous embodiments that can be made within the scope of the appending claims. It is contemplated that the configurations of nuclear gauges and the methods of configuration and calibration of the same can comprise numerous configurations other than those specifically disclosed. The scope of a patent issuing from this disclosure will be defined by these appending claims.

What is claimed is:

1. A method for calibrating a nuclear gauge of the having a source, the method comprising:
   providing a nuclear gauge comprising a radiation source, the radiation source being coupled with a computing system with a machine readable program stored thereon containing a calibration routine;
   wherein an operator places the gauge on one or more specified blocks to adjust the source within each of the one or more specified blocks to one or more specified positions to initiate a count;
   determining that the source is at each of the one or more specified positions before each count begins;
   selecting the proper counting times before each count begins by the program on the nuclear gauge based on each of the one or more specified positions of the source to obtain calibration information;
   obtaining counts at each of the one or more specified positions;
   storing the counts within the computing system of the nuclear gauge; and
   calculating, by the nuclear gauge, for each of the one or more specified positions, calibration coefficients.

2. The method of claim 1, wherein at least one position in each block is a backscatter position.

3. The method of claim 1, wherein at least one block of the one or more specified blocks is a magnesium, aluminum, or magnesium-aluminum block.

4. The method of claim 3, wherein the one or more specified blocks comprise one to five blocks.

5. The method of claim 4, further comprising repeating the steps of determining that the source is at each of the one or more specified positions, selecting the proper counting times, obtaining counts and storing the counts within the computing system of the nuclear gauge for multiple positions of the source within multiple blocks.

6. The method of claim 1, wherein selecting the proper counting times comprises automatically selecting the proper counting times.

7. The method of claim 1, further comprising, at the nuclear gauge, performing a quality control routine on the gauge to confirm calibration.

8. The method of claim 1, wherein the quality control routine comprises using previously downloaded standard information stored in the computing system of the gauge to perform diagnostics on the gauge.

9. The method of claim 1, wherein the diagnostics include analyzing the coefficients of each curve for slope, count rate, precision and standard deviation.

10. The method of claim 1, further comprising calculating internal to the gauge calibration curves for one or more positions.

11. The method of claim 1, wherein results are wirelessly transmitted to a local computer, network, server, or cloud for record storage.

12. The method of claim 1, wherein the calibration routine is configured to automatically select the proper counting times before each count begins.

13. A nuclear gauge comprising:
   a radiation source; and
   a computing system having a machine readable program stored thereon containing a calibration routine, the computing system being coupled with the source, wherein the calibration routine is configured to:
      determine that the source is at each of one or more specified positions before each of one or more counts begins, wherein a count is initiated when an operator places the gauge on one or more specified blocks and adjusts the source, within each of the one or more specified blocks, to one or more specified positions, and initiates the count by user input;
      select the proper counting times before each count begins, by the program on the nuclear gauge, based on each of the one or more specified positions of the source to obtain calibration information;
      obtain counts at each of the one or more specified positions;
      store the counts within the computing system of the nuclear gauge; and
      calculate, for each of the one or more specified positions, calibration coefficients.

14. The gauge of claim 13, wherein at least one position in each block is a backscatter position.

15. The gauge of claim 13, wherein at least one block of the one or more specified blocks is a magnesium, aluminum, or magnesium-aluminum block.

16. The gauge of claim 15, wherein the one or more specified blocks comprise one to five blocks.

17. The gauge of claim 16, wherein the computing system is further configured for repeating the steps of determining that the source is at each of one or more specified positions, selecting the proper counting times, and storing the counts within the computing system for multiple positions of the source within the multiple density blocks.

18. The gauge of claim 13, wherein the nuclear gauge is further configured for performing a quality control routine on the gauge to confirm the calibration.

19. The gauge of claim 13, wherein the quality control routine comprises using previously downloaded standard information stored in the computing system of the gauge to perform diagnostics on the gauge.

20. The gauge of claim 13, wherein the diagnostics include analyzing the coefficients of each curve for slope, count rate, precision and standard deviation.

21. The gauge of claim 13, wherein the computing system is further configured for calculating calibration curves for one or more positions.

22. The gauge of claim 13, wherein results are wirelessly transmitted to a local computer, network, server, or cloud for record storage.

23. The gauge of claim 22 whereby at least one of owner information, serial number, date, time, location, and notes are stored and recorded remotely from the gauge.

* * * * *